United States Patent
Sugimoto et al.

(10) Patent No.: US 8,120,022 B2
(45) Date of Patent: Feb. 21, 2012

(54) LIGHT EMITTING DEVICE MATERIAL AND LIGHT EMITTING DEVICE

(75) Inventors: Kazunori Sugimoto, Otsu (JP); Tsuyoshi Tominaga, Otsu (JP)

(73) Assignee: Toray Industries, Inc., Tokyo (JP)

( * ) Notice: Subject to any disclaimer, the term of this patent is extended or adjusted under 35 U.S.C. 154(b) by 201 days.

(21) Appl. No.: 12/670,681

(22) PCT Filed: Jul. 16, 2008

(86) PCT No.: PCT/JP2008/062786
§ 371 (c)(1),
(2), (4) Date: Jan. 26, 2010

(87) PCT Pub. No.: WO2009/016964
PCT Pub. Date: Feb. 5, 2009

(65) Prior Publication Data
US 2010/0187520 A1 Jul. 29, 2010

(30) Foreign Application Priority Data
Jul. 27, 2007 (JP) .................................. 2007-195505

(51) Int. Cl.
*H01L 51/00* (2006.01)
*H01L 51/30* (2006.01)
(52) U.S. Cl. ............. 257/40; 257/E51.018; 257/E51.026
(58) Field of Classification Search .................... 257/40, 257/E51.018, E51.026
See application file for complete search history.

(56) References Cited

U.S. PATENT DOCUMENTS

| | | | |
|---|---|---|---|
| 7,115,899 B2 * | 10/2006 | Uckert | 257/40 |
| 7,119,360 B2 * | 10/2006 | Mullen et al. | 257/40 |
| 2010/0133519 A1 * | 6/2010 | Chen et al. | 257/40 |
| 2011/0073850 A1 * | 3/2011 | Otsu et al. | 257/40 |
| 2011/0198575 A1 * | 8/2011 | Radu et al. | 257/40 |
| 2011/0203667 A1 * | 8/2011 | Liao et al. | 136/263 |
| 2011/0227051 A1 * | 9/2011 | Suzuki et al. | 257/40 |

FOREIGN PATENT DOCUMENTS

| | | |
|---|---|---|
| JP | 05-017765 | 1/1993 |
| JP | 2000-113985 | 4/2000 |
| JP | 2001-291590 | 10/2001 |
| JP | 2003-086380 | 3/2003 |
| JP | 2003-142263 | 5/2003 |
| JP | 2005-075944 | 3/2005 |
| JP | 2008-184566 | 8/2008 |
| WO | WO00/40586 | 7/2000 |
| WO | WO2006/100896 A1 | 9/2006 |
| WO | 2007-039406 | 2/2007 |
| WO | WO2007/018007 A1 | 2/2007 |
| WO | WO2007/145136 A1 | 12/2007 |

OTHER PUBLICATIONS

International Search Report dated Oct. 14, 2008, application No. PCT/JP2008/062786.
C.W. Tang and S.A. Van Slyke, "Organic Electroluminescent Diodes", Appl. Phys. Lett. 51 (12) Sep. 21, 1987, pp. 913-915.

* cited by examiner

*Primary Examiner* — Victor A Mandala
(74) *Attorney, Agent, or Firm* — RatnerPrestia

(57) ABSTRACT

Disclosed is a light emitting device material characterized by containing a specific fluorine compound. This light emitting device material enables to obtain a light emitting device having high luminous efficiency, excellent color purity and excellent durability. Also disclosed is a light emitting device using such a light emitting device material.

9 Claims, No Drawings

LIGHT EMITTING DEVICE MATERIAL AND LIGHT EMITTING DEVICE

This application is a U.S. National Phase Application of PCT International Application No. PCT/JP2008/062786, filed Jul. 16, 2008, which claims priority to Japanese Patent Application No. 2007-195505, filed Jul. 27, 2007, the content of each of these applications being incorporated by reference herein in their entirety for all purposes.

BACKGROUND OF THE INVENTION

1. Field of the Invention

The present invention relates to a light emitting device material which is useful as a fluorescent dye and a charge transporting material, and a light emitting device using the same. The light emitting device of the present invention can be applied to the fields of display elements, flat panel displays, backlights, illuminations, interiors, signs, billboards, electrophotographic machines, optical signal generators and the like.

2. Description of the Background Art

In recent years, there have actively been conducted researches of an organic thin-film light emitting device that emits light when an electron injected from a cathode and a hole injected from an anode recombine in an organic luminous body interposed between the electrodes. Intense interest has been shown toward this light emitting device because of such a feature that it is thin and capable of emitting high-luminance light under a low driving voltage and emitting multicolor light through selection of an emissive material.

Since C. W. Tang et al. of Eastman Kodak Company showed that an organic thin-film light emitting device emitted light at a high luminance, many research institutes have studied this technology. The typical structure of an organic thin-film light emitting device proposed by a research group of Eastman Kodak Company is such that a hole-transporting diamine compound, an emissive layer made of tris(8-quinolinolato)aluminum(III), and a cathode made of a Mg:Ag alloy are formed sequentially on an ITO glass substrate, and the device was able to emit green light of 1,000 cd/m² at a driving voltage of about 10 V (see Applied Physics Letters, USA, 1987, Vol. 51, No. 12, pp. 913-915).

One of the greatest problems with organic thin-film light emitting devices is to obtain luminance efficiency, color purity, and durability of a device at satisfactory levels simultaneously. With respect to a blue light emitting device, there are few blue emissive materials capable of providing a device that is excellent in luminance efficiency and color purity and has high reliability. For example, there have been disclosed technologies using, as a blue dopant material, a styrylamine derivative (see Japanese Unexamined Patent Publication No. 5-17765), a perylene derivative (see Japanese Unexamined Patent Publication No. 2003-86380), and an anthracene derivative (see International Publication No. 00/40586 Pamphlet). Moreover, technologies using a fluorene compound (see Japanese Unexamined Patent Publication No. 2007-39406 and International Publication No. 06/100896 pamphlet) for a blue light emitting device have been disclosed. However, all the technologies are insufficient in luminance efficiency, color purity, and durability.

SUMMARY OF THE INVENTION

The present invention provides a light emitting device material which makes it possible to produce a light emitting device being high in luminance efficiency and excellent in color purity and durability, and a light emitting device using the same.

The present invention is directed to a light emitting device material containing a fluorene compound represented by the general formula (1):

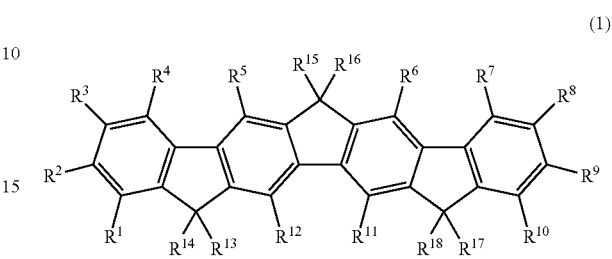

wherein $R^1$ to $R^{18}$ each may be the same or different and are selected from among hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a cyano group, an amino group, a silyl group, and $-P(=O)R^{19}R^{20}$, $R^{19}$ and $R^{20}$ are each selected from among an aryl group and a heteroaryl group, adjacent substituents among $R^1$ to $R^{18}$ may be combined with each other to form a ring, provided that at least one of $R^1$ to $R^{12}$ is a substituent represented by the following general formula (2):

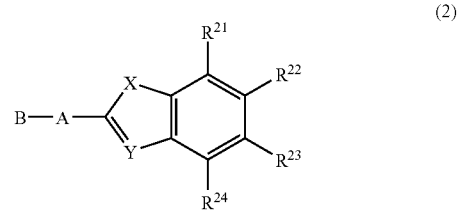

wherein $R^{21}$ to $R^{24}$ each may be the same or different and are selected from among hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a cyano group, an amino group, and a silyl group, adjacent substituents among $R^{21}$ to $R^{24}$ may be combined with each other to form a ring, A is selected from among a single bond, an arylene group, and a heteroarylene group, B is used for linkage to $R^1$ to $R^{12}$, X is an oxygen atom or a sulfur atom, and Y is selected from among the following groups:

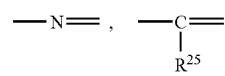

wherein $R^{25}$ is selected from among hydrogen, an alkyl group, a cycloalkyl group, a heterocyclic group, an alkenyl group, a cycloalkenyl group, an alkynyl group, an aryl group, and a heteroaryl group.

Moreover, embodiments of the present invention are directed to a light emitting device comprising an anode, a cathode, and at least an emissive layer, the emissive layer being capable of emitting light by electric energy, wherein the emissive layer includes the fluorene compound represented by the general formula (1).

According to the present invention, a light emitting device that is high in luminance efficiency and excellent in at least one of color purity and durability is obtained.

DETAILED DESCRIPTION OF THE INVENTION

The fluorene compound represented by the following general formula (1) is described in detail.

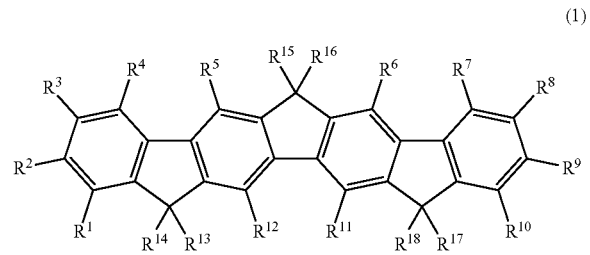

(1)

wherein $R^1$ to $R^{18}$ each may be the same or different and are selected from among hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a cyano group, an amino group, a silyl group, and $-P(=O)R^{19}R^{20}$, $R^{19}$ and $R^{20}$ are each selected from among an aryl group and a heteroaryl group, adjacent substituents among $R^1$ to $R^{18}$ may be combined with each other to form a ring, provided that at least one of $R^1$ to $R^{12}$ is a substituent represented by the following general formula (2):

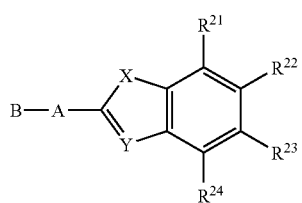

(2)

wherein $R^{21}$ to $R^{24}$ each may be the same or different and are selected from among hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a cyano group, an amino group, and a silyl group, adjacent substituents among $R^{21}$ to $R^{24}$ may be combined with each other to form a ring, A is selected from among a single bond, an arylene group, and a heteroarylene group, B is used for linkage to $R^1$ to $R^{12}$, X is an oxygen atom or a sulfur atom, and Y is selected from among the following groups:

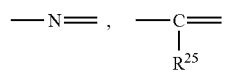

wherein $R^{25}$ is selected from among hydrogen, an alkyl group, a cycloalkyl group, a heterocyclic group, an alkenyl group, a cycloalkenyl group, an alkynyl group, an aryl group, and a heteroaryl group.

Among these substituents, the alkyl group denotes a saturated aliphatic hydrocarbon group, such as a methyl group, an ethyl group, an n-propyl group, an isopropyl group, an n-butyl group, a sec-butyl group, or a tert-butyl group, and it may or may not have a substituent. When substituted, the additional substituent is not particularly limited and includes, for example, an alkyl group, an aryl group, and a heteroaryl group, and this respect is common to the following description. The number of carbon atoms of the alkyl group is not particularly limited, and it is usually preferably 1 or more and 20 or less and more preferably is in the range of 1 or more and 8 or less in view of availability and cost.

The cycloalkyl group denotes a saturated alicyclic hydrocarbon group, such as cyclopropyl, cyclohexyl, norbornyl, or adamantyl, and it may or may not have a substituent. The number of carbon atoms of the cycloalkyl group is not particularly limited and is usually preferably in the range of 3 or more and 20 or less in view of availability and cost.

The heterocyclic group denotes an aliphatic ring having an atom other than carbon in the ring, such as a pyran ring, a piperidine ring, or a cyclic amide, and it may or may not have a substituent. The number of carbon atoms of the heterocyclic group is not particularly limited and is usually preferably in the range of 2 or more and 20 or less in view of availability and cost.

The alkenyl group denotes an unsaturated aliphatic hydrocarbon group containing a double bond, such as a vinyl group, an allyl group, or a butadienyl group, and it may or may not have a substituent. The number of carbon atoms of the alkenyl group is not particularly limited and is usually preferably in the range of 2 or more and 20 or less in view of availability and cost.

The cycloalkenyl group denotes an unsaturated alicyclic hydrocarbon group containing a double bond, such as a cyclopentenyl group, a cyclopentadienyl group, or a cyclohexenyl group, and it may or may not have a substituent. The number of carbon atoms of the cycloalkenyl group is not particularly limited and is usually preferably in the range of 3 or more and 20 or less in view of availability and cost.

The alkynyl group denotes an unsaturated aliphatic hydrocarbon group containing a triple bond, such as an ethynyl group, and it may or may not have a substituent. The number of carbon atoms of the alkynyl group is not particularly limited and is usually preferably in the range of 2 or more and 20 or less in view of availability and cost.

The alkoxy group denotes a functional group to which an aliphatic hydrocarbon group has been attached via an ether bond, such as a methoxy group, an ethoxy group, or a propoxy group, and the aliphatic hydrocarbon group may or may not have a substituent. The number of carbon atoms of the alkoxy group is not particularly limited and is usually preferably in the range of 1 or more and 20 or less in view of availability and cost.

The alkylthio group is a group resulting from replacement of an oxygen atom of the ether bond of an alkoxy group by a sulfur atom. The hydrocarbon group in the alkylthio group may or may not have a substituent. The number of carbon atoms of the alkylthio group is not particularly limited and is usually preferably in the range of 1 or more and 20 or less in view of availability and cost.

The aryl ether group denotes a functional group to which an aromatic hydrocarbon group has been attached via an ether bond, such as a phenoxy group, and the aromatic hydrocarbon group may or may not have a substituent. The number of carbon atoms of the aryl ether group is not particularly limited and is usually preferably in the range of 6 or more and 40 or less in view of availability and cost.

The aryl thioether group is a group resulting from replacement of an oxygen atom of the ether bond of an aryl ether group by a sulfur atom. The aromatic hydrocarbon group in the aryl thioether group may or may not have a substituent. The number of carbon atoms of the aryl thioether group is not particularly limited and is usually preferably in the range of 6 or more and 40 or less in view of availability and cost.

The aryl group denotes an aromatic hydrocarbon group, such as a phenyl group, a naphtyl group, a biphenyl group, a phenanthryl group, a terphenyl group, or a pyrenyl group. The aryl group may or may not have a substituent. The number of carbon atoms of the aryl group is not particularly limited and is usually preferably in the range of 6 or more and 40 or less in view of availability and cost.

The heteroaryl group denotes a cyclic aromatic group having one atom or two or more atoms other than carbon in the ring, such as a furanyl group, a thiophenyl group, a pyrrolyl group, a benzofuranyl group, a benzothiophenyl group, an indolyl group, a pyridyl group, or a quinolinyl group, and it may or may not have a substituent. The number of carbon atoms of the heteroaryl group is not particularly limited and is usually preferably in the range of 2 or more and 30 or less in view of availability and cost.

The halogen denotes fluorine, chlorine, bromine, or iodine. The cyano group, the amino group, and the —P(=O)$R^{19}R^{20}$ each may or may not have a substituent. $R^{19}$ and $R^{20}$ are each selected from among an aryl group and a heteroaryl group.

The silyl group denotes a functional group having a bond to a silicon atom, such as a trimethylsilyl group, and it may or may not have a substituent. The number of carbon atoms of the silyl group is not particularly limited and is usually preferably in the range of 3 or more and 20 or less in view of availability and cost. The number of silicon atoms is usually preferably 1 or more and 6 or less in view of availability and cost.

Examples of the substituent each of the aforementioned groups may have include the alkyl groups, cycloalkyl groups, aryl groups, heteroaryl groups, and halogens.

Any of adjacent two substituents (for example, $R^1$ and $R^2$ in the general formula (1)) may be combined with each other to form a conjugated or non-conjugated fused ring. The constituent element of the fused ring may include, in addition to carbon, elements selected from among nitrogen, oxygen, sulfur, phosphorus and silicon. The fused ring may further be fused with another ring.

As to the fluorene compound represented by the general formula (1), it is preferable that particularly $R^{13}$ to $R^{18}$ be each a group selected from among an alkyl group, an aryl group, and a heteroaryl group because the interaction of the fluorene compounds is inhibited, so that it becomes possible to emit light at high efficiency. In this case, an equal effect is obtained with any substituent of an alkyl group, an aryl group, and a heteroaryl group.

The skeleton that the fluorene compound has is not particularly limited and preferred specific examples thereof include the following:

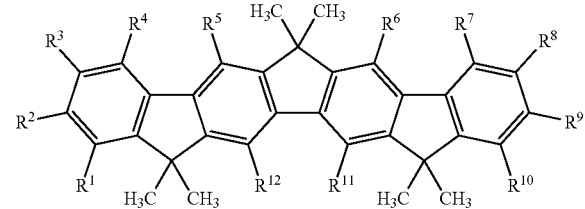

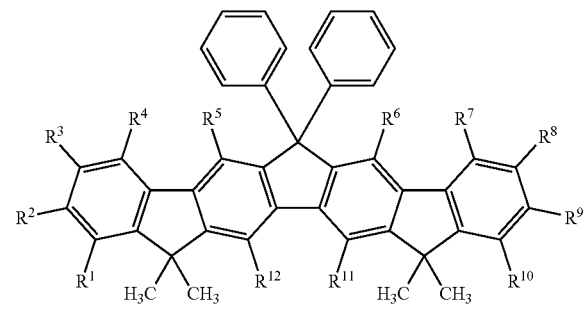

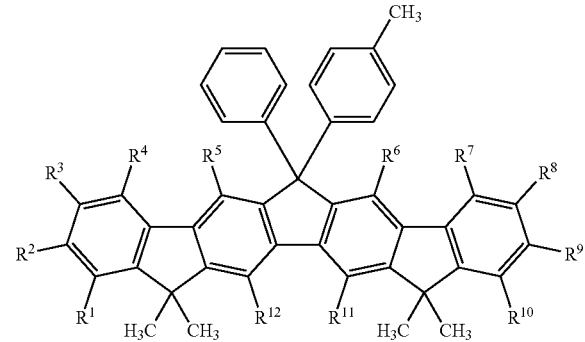

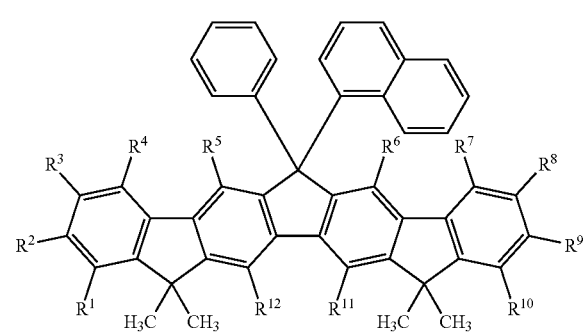

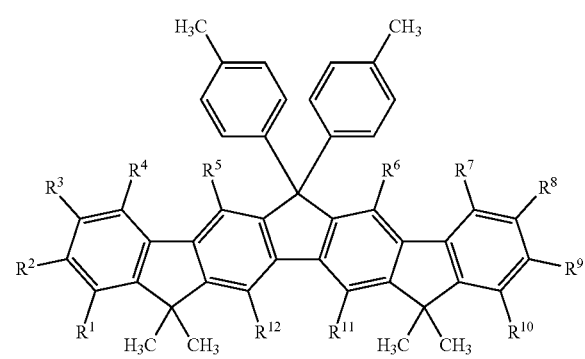

-continued

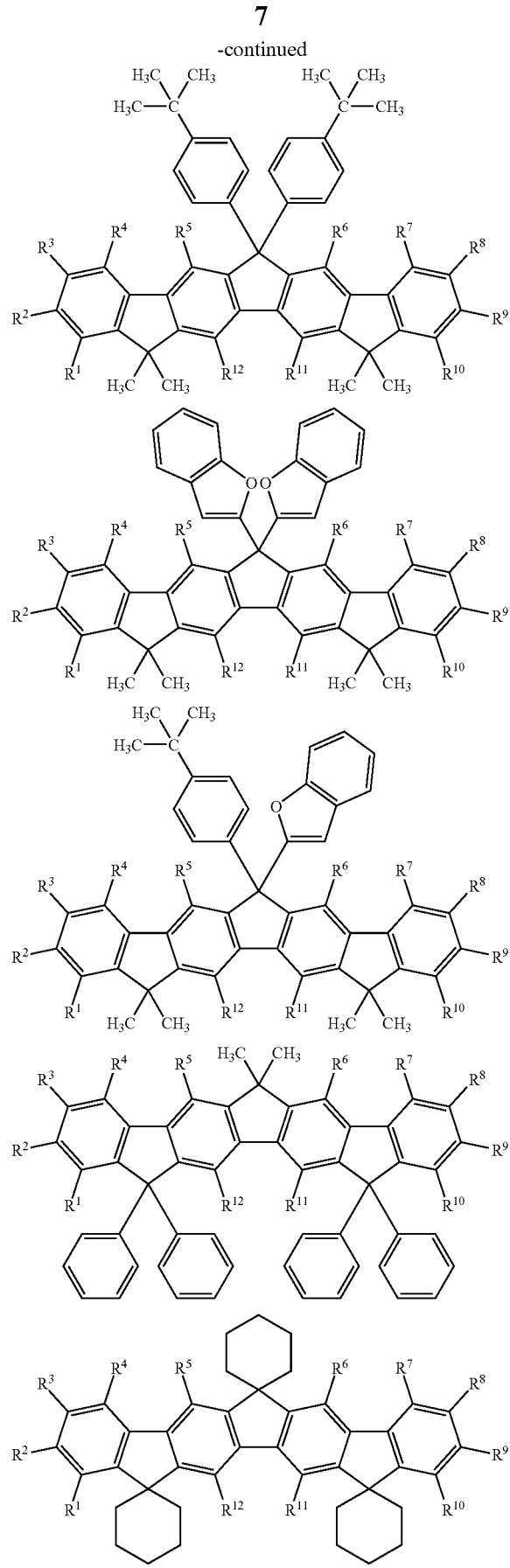

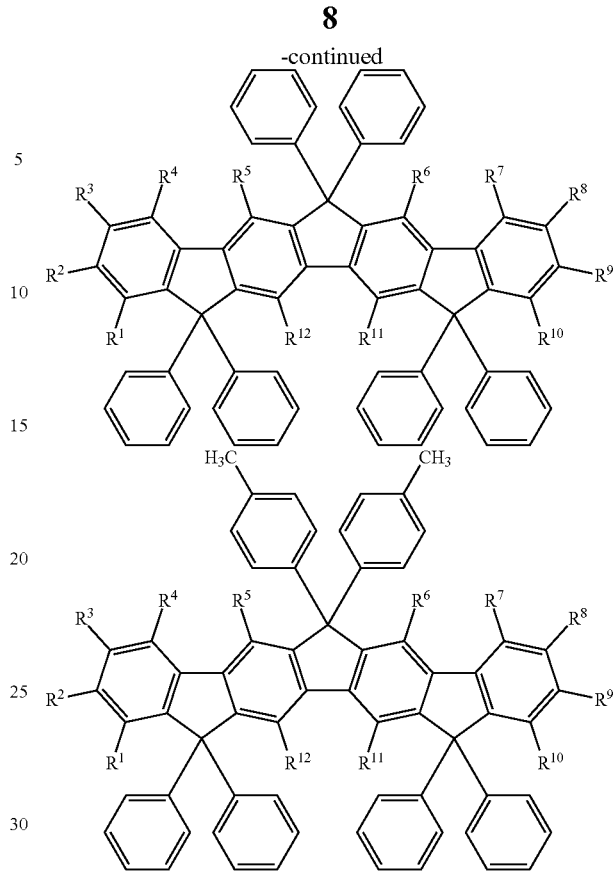

The fluorene compound of embodiments of the present invention represented by the general formula (1) is high in luminance efficiency and color purity because of the fact that at least one of $R^1$ to $R^{12}$ is a group represented by the general formula (2).

In the general formula (2), A is selected from among a single bond, an arylene group, and a heteroarylene group, and particularly, it is preferable that A be a single bond as in a group represented by the general formula (3) because higher luminance efficiency is obtained, the Stokes' shift becomes narrower, and the color purity is excellent.

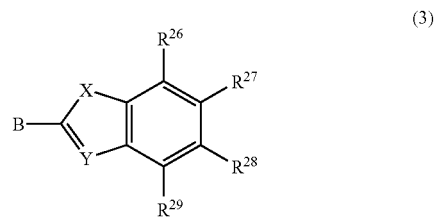

(3)

$R^{26}$ to $R^{29}$ each may be the same or different and are selected from among hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a cyano group, an amino group, and a silyl group. Adjacent substituents among $R^{26}$ to $R^{29}$ may be combined with each other to form a ring. B is used for linkage to $R^1$ to $R^{12}$. X is an oxygen atom or a sulfur atom. Y is selected from among the following groups:

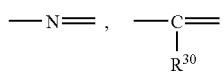

wherein $R^{30}$ is selected from among hydrogen, an alkyl group, a cycloalkyl group, a heterocyclic group, an alkenyl group, a cycloalkenyl group, an alkynyl group, an aryl group, and a heteroaryl group.

The group represented by the general formula (3) denotes a group selected from among a benzofuryl group (when X is an oxygen atom and Y is —$CR^{30}$=), a benzothienyl group (when X is a sulfur atom and Y is —$CR^{30}$=), a benzoxazolyl group (when X is an oxygen atom and Y is —N=), and a benzothiazolyl group (when X is a sulfur atom and Y is —N=). Among them, a benzoxazolyl group or a benzothiazolyl group, in which Y is a nitrogen atom (—N=), is particularly preferable because higher luminance efficiency is obtained and the durability of a light emitting device is enhanced.

A case where X is a sulfur atom is preferable because the heat resistance increases in comparison to the case of an oxygen atom and a film can be formed stably by vacuum deposition, for example.

The groups represented by the general formulae (2) to (3) are not particularly limited, and preferred specific examples thereof include the following:

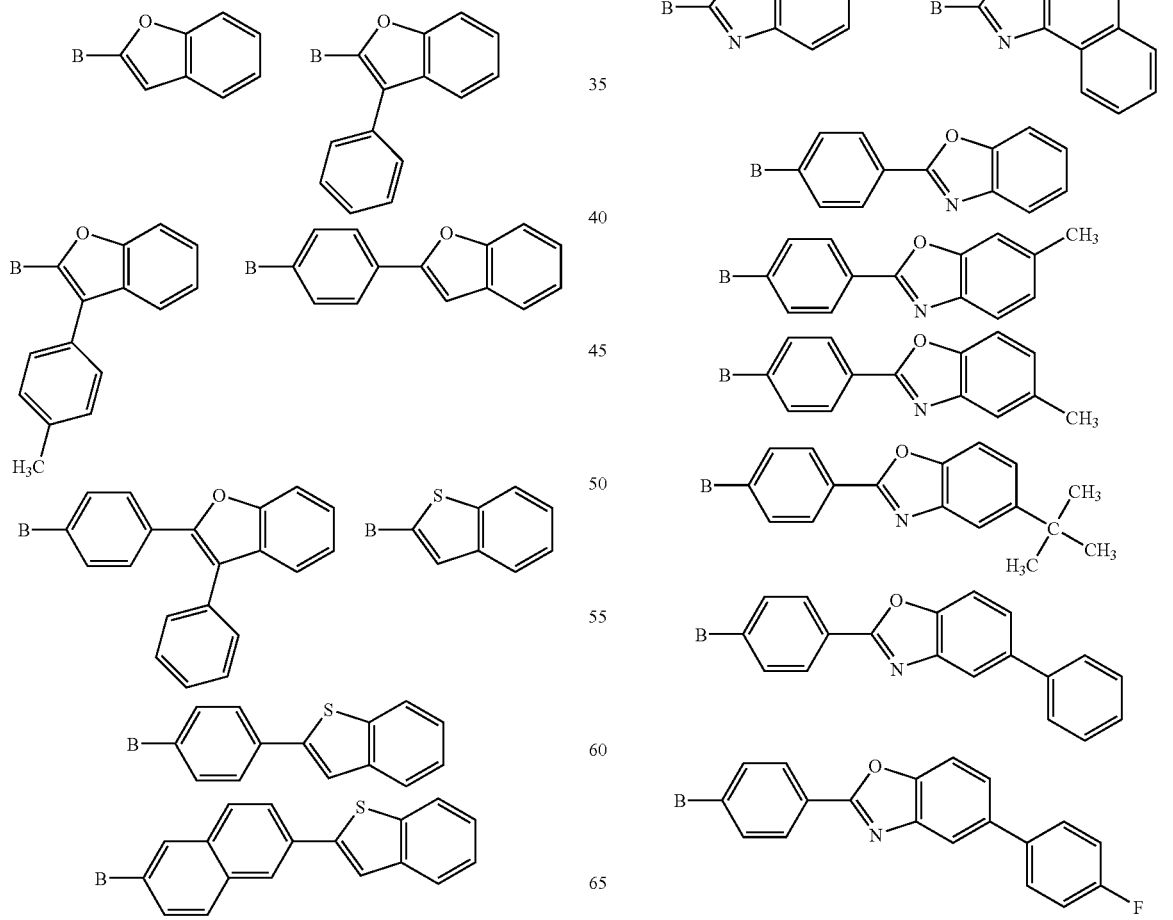

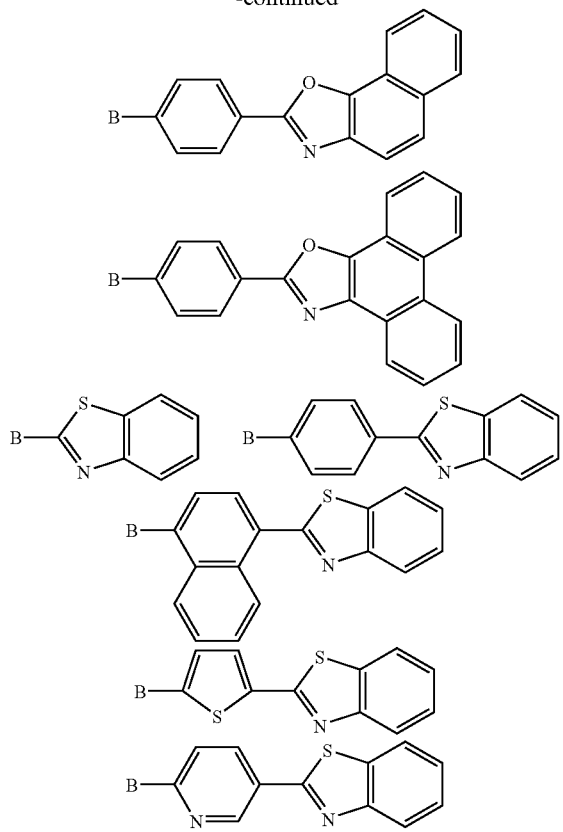
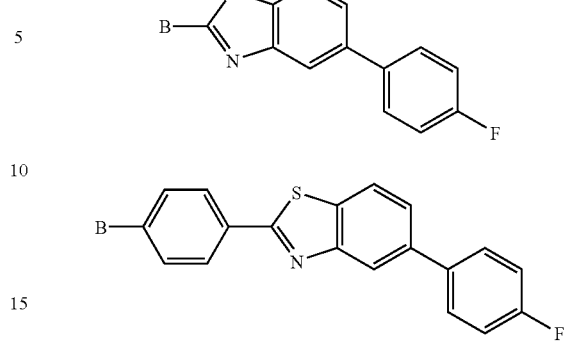

In view of the availability and the easiness of synthesis of raw materials and because high luminance efficiency can be obtained, it is preferable that at least one of $R^2$ and $R^9$ of the general formula (1) be any of the groups represented by the general formulae (2) to (3). Moreover, it is preferable that both $R^2$ and $R^9$ be any of the groups represented by the general formulae (2) to (3) because the durability of a light emitting device is enhanced.

If a group other than the groups represented by the general formulae (2) to (3) is introduced as $R^2$ or $R^9$, the group is preferably an aryl group or a heteroaryl group in view of high luminance efficiency and durability enhancement.

The aforementioned fluorene compound is not particularly limited and specific examples thereof include the following:

[1]

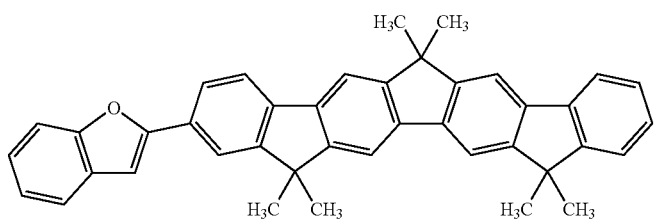

[2]

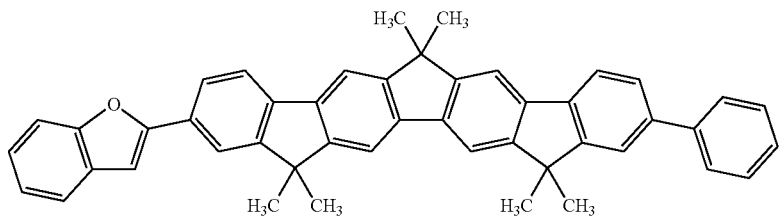

[3]

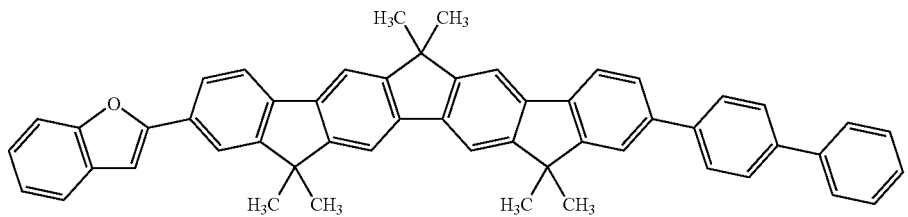

-continued
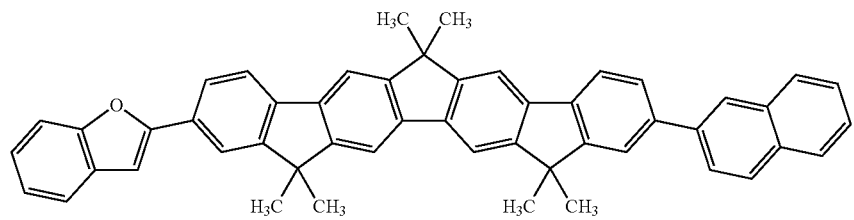
[4]
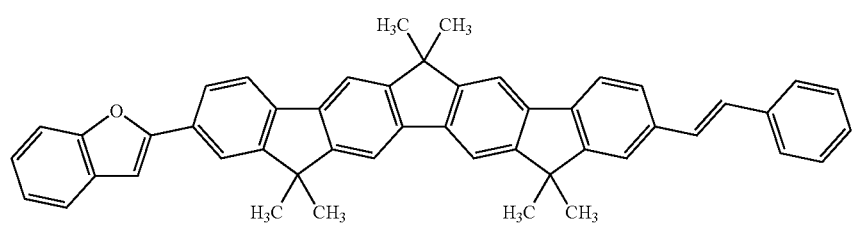
[5]
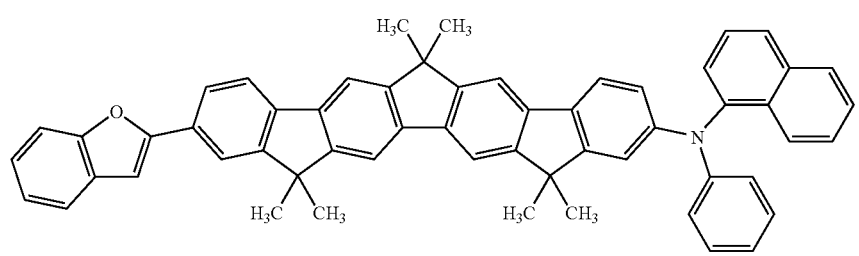
[6]
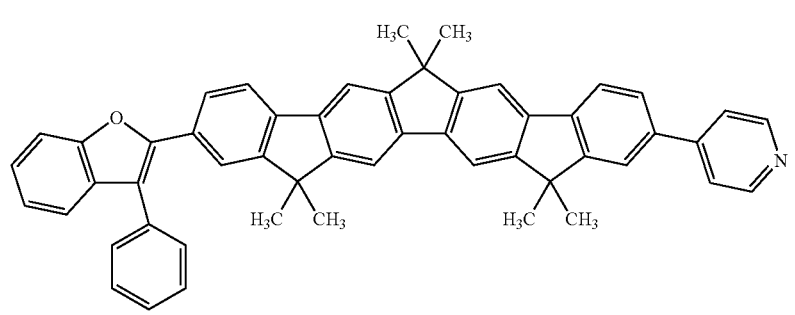
[7]
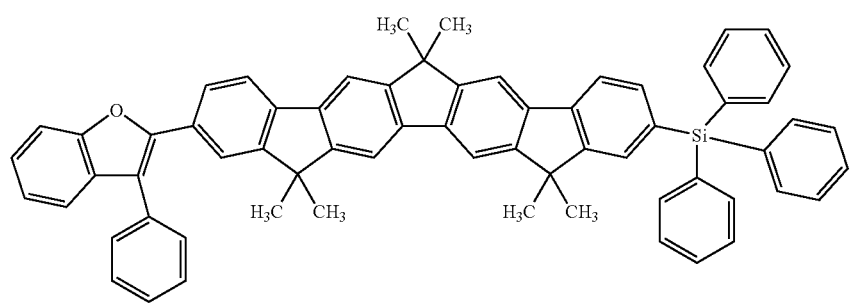
[8]
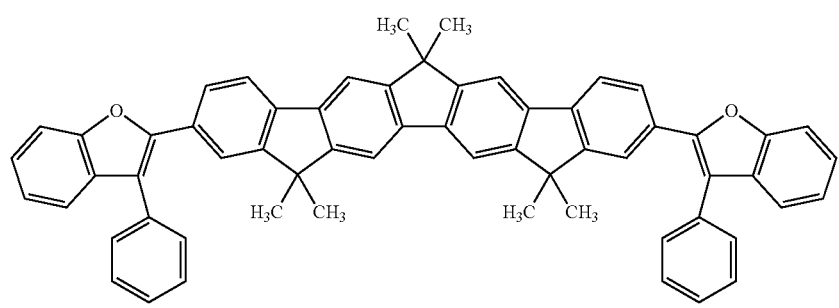
[9]

-continued
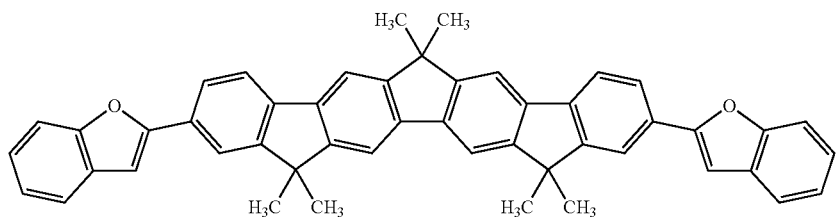
[10]
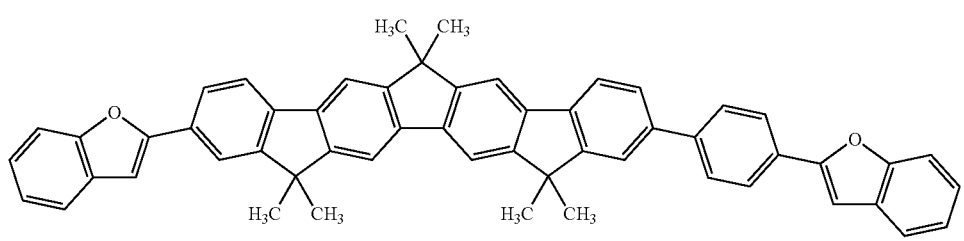
[11]
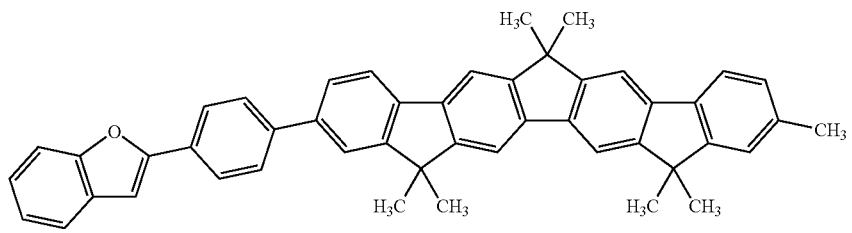
[12]
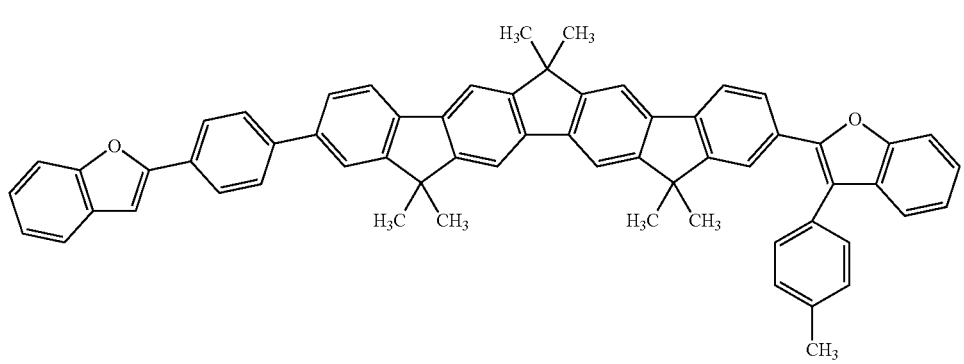
[13]
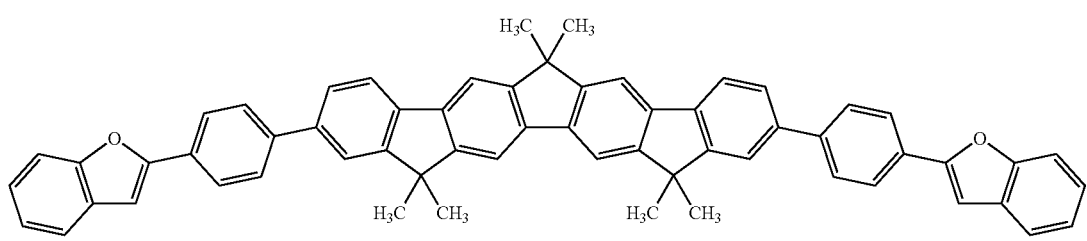
[14]
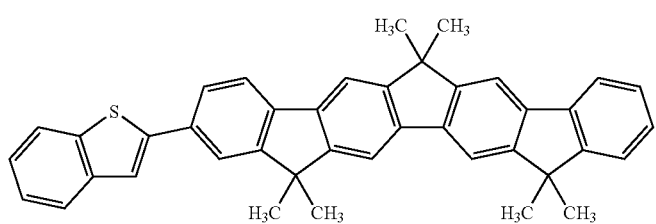
[15]

-continued
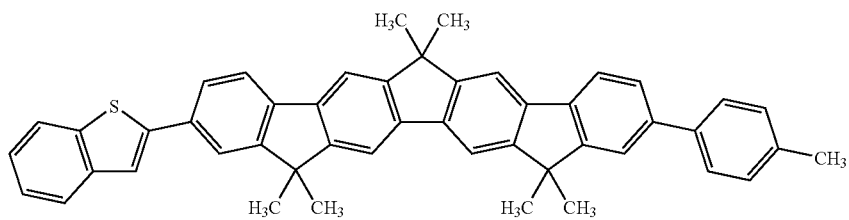
[16]
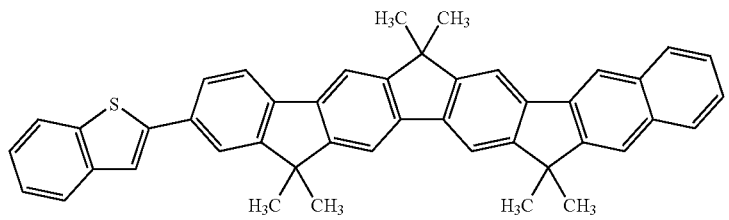
[17]
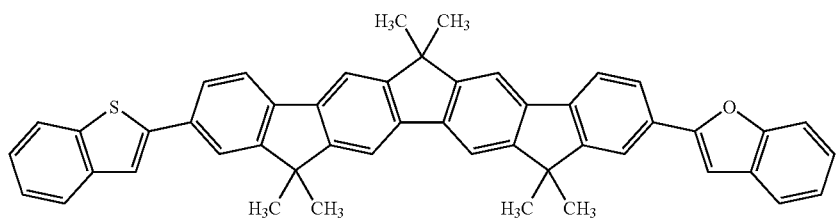
[18]
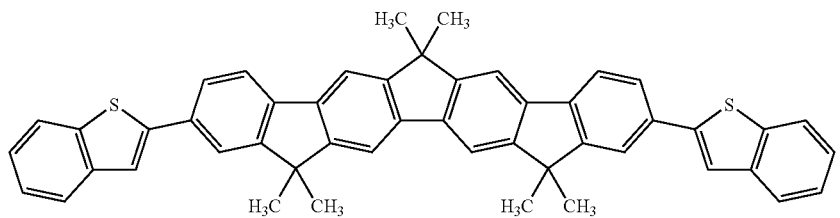
[19]
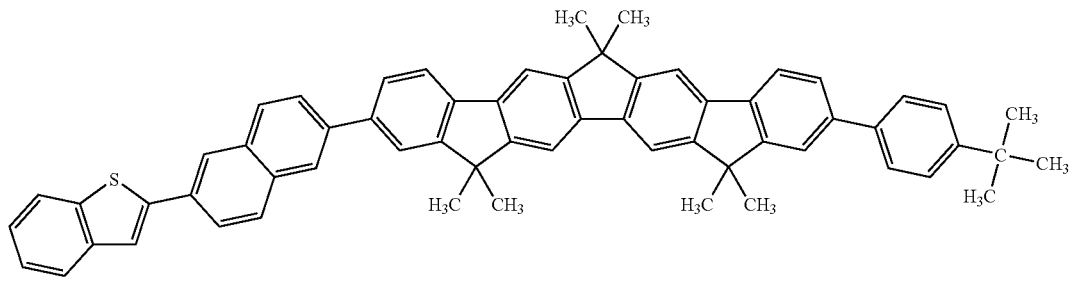
[20]
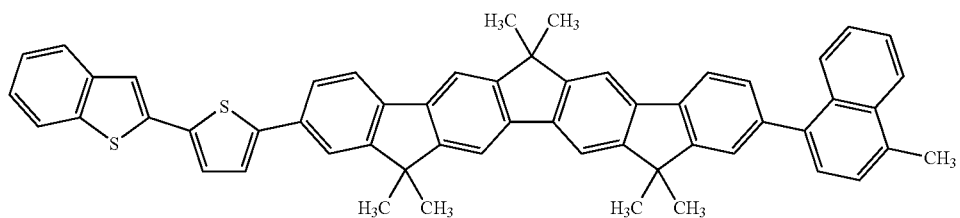
[21]
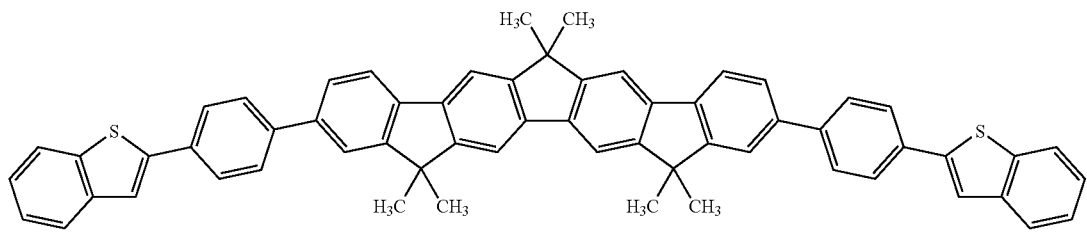
[22]

-continued
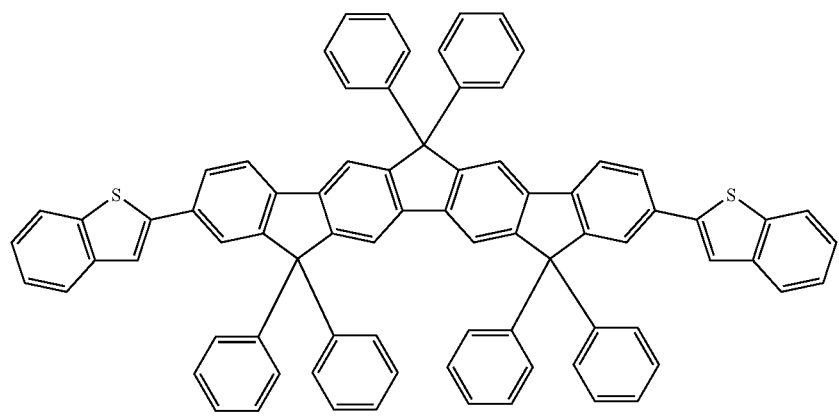
(23)
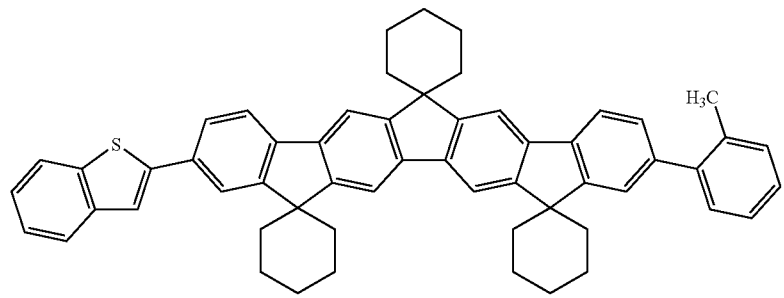
(24)
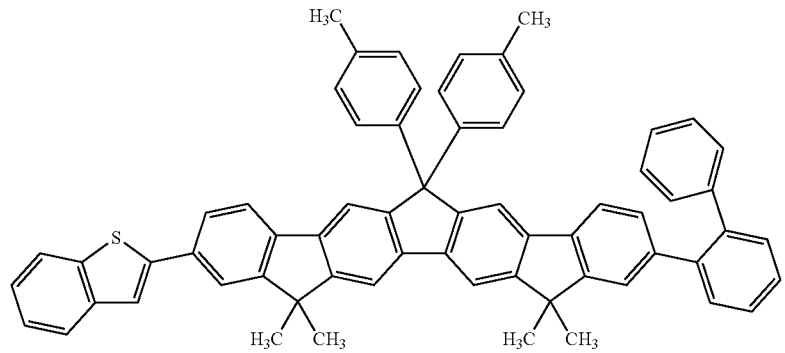
(25)
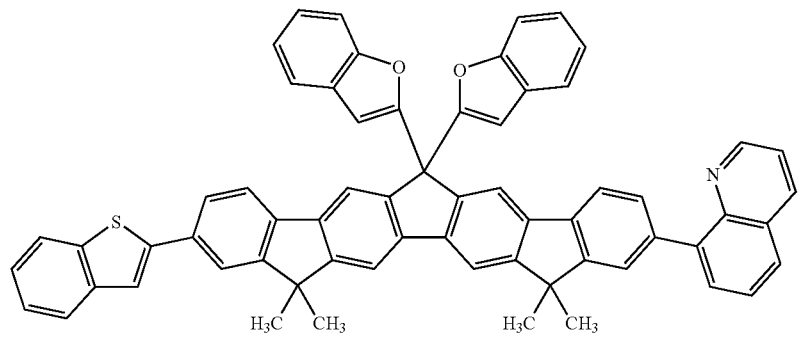
(26)
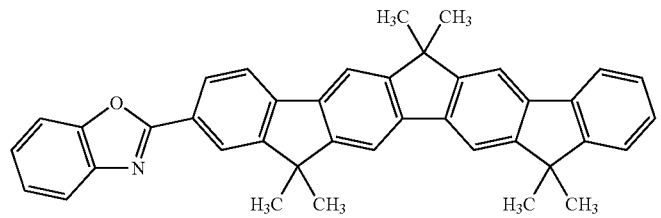
(27)

(28)
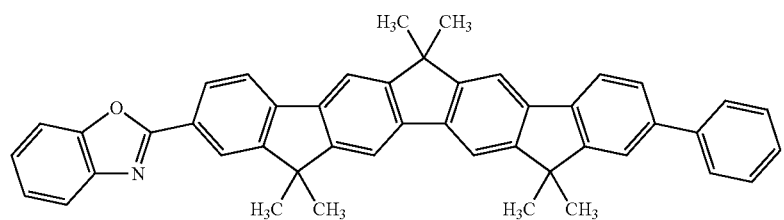
(29)
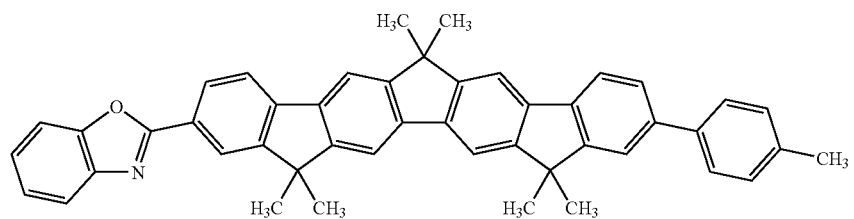
(30)
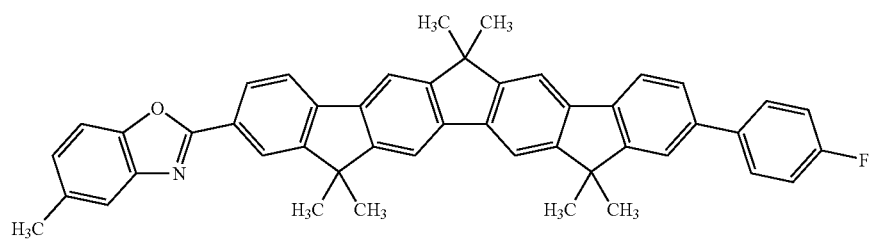
(31)
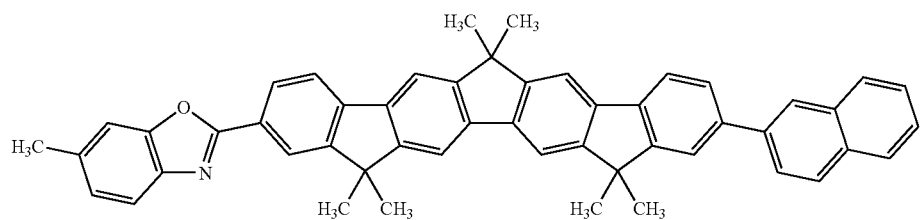
(32)
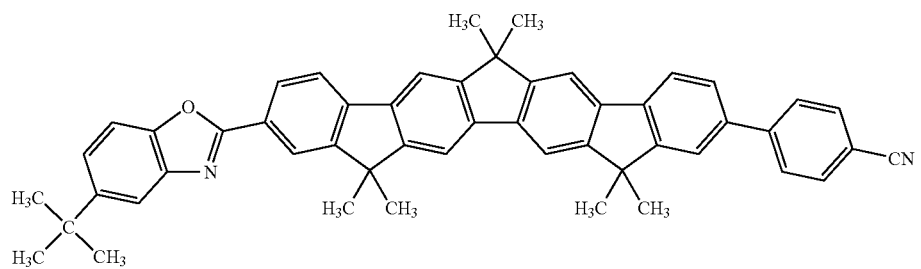
(33)
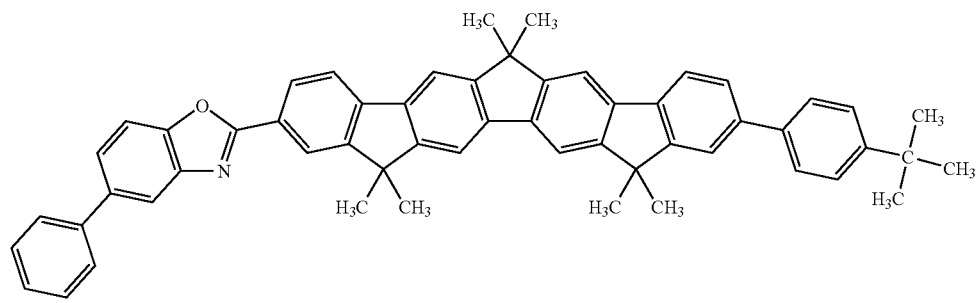

(34)
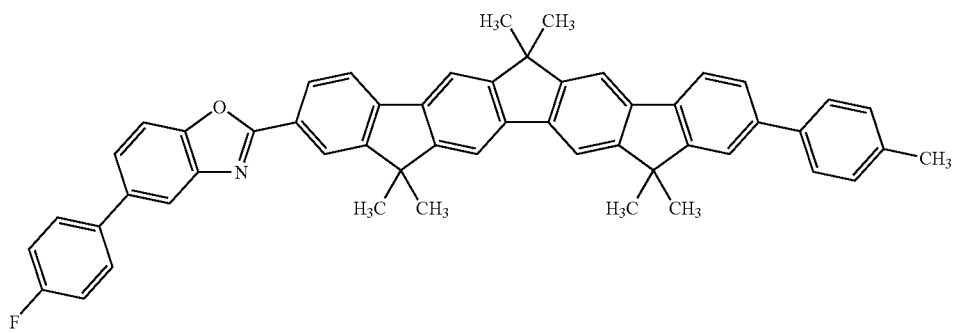
(35)
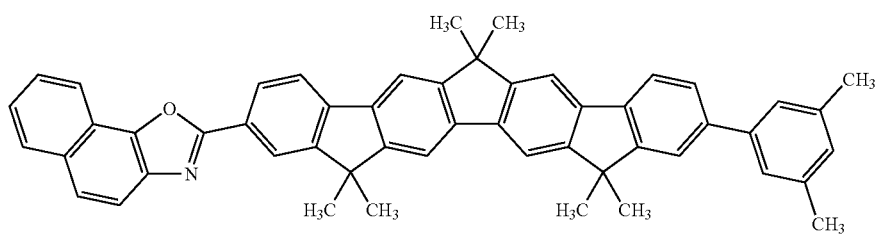
(36)
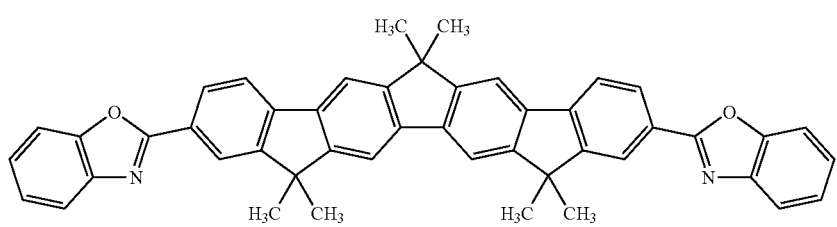
(37)
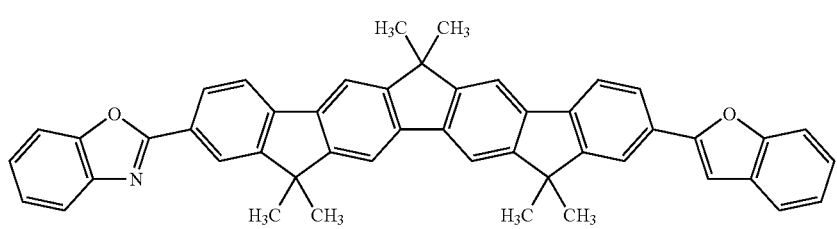
(38)
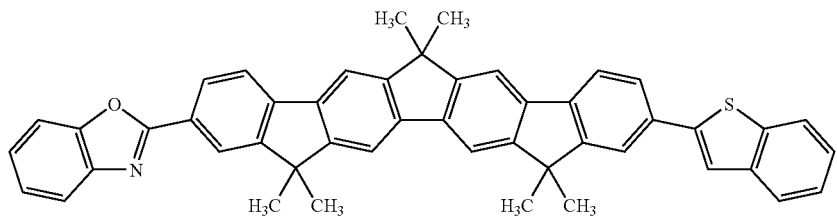
(39)
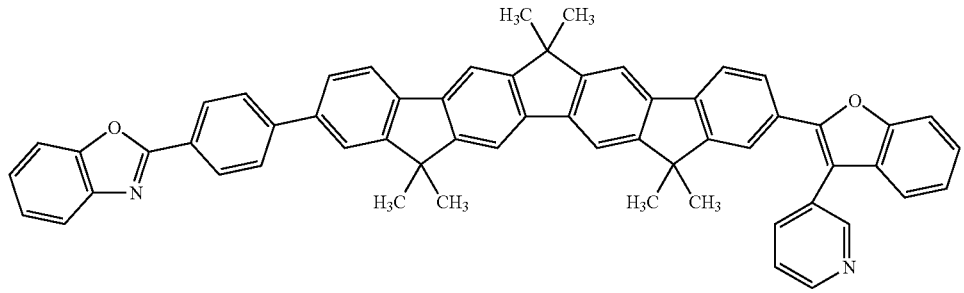

-continued
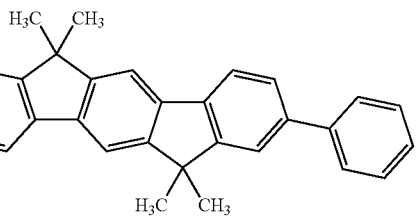
[40]
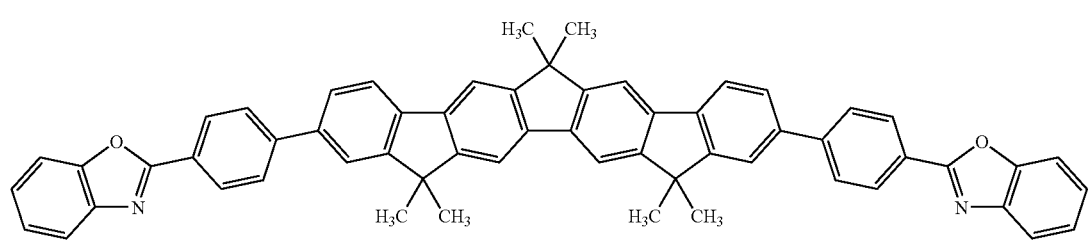
[41]
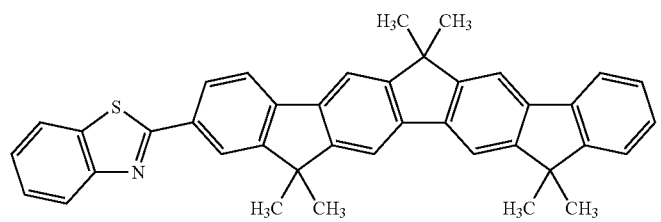
[42]
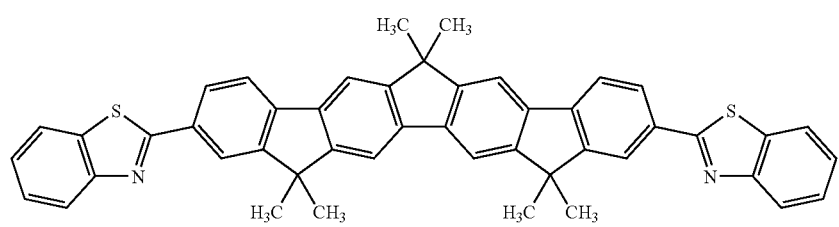
[43]
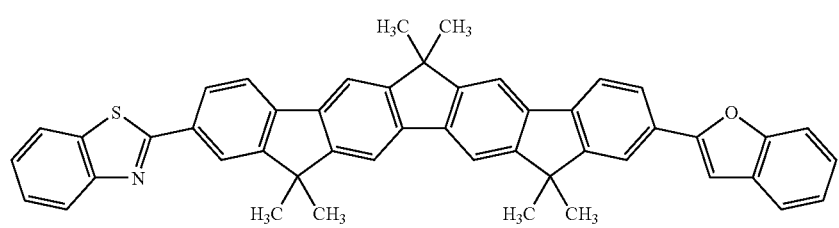
[44]
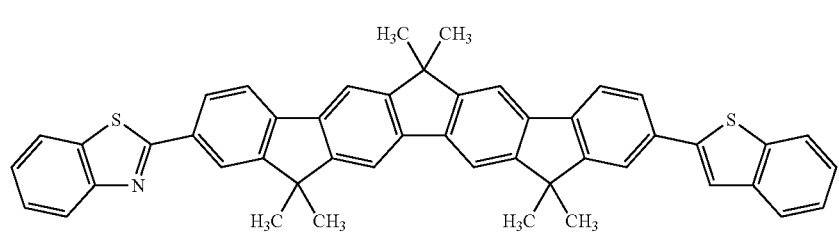
[45]

-continued
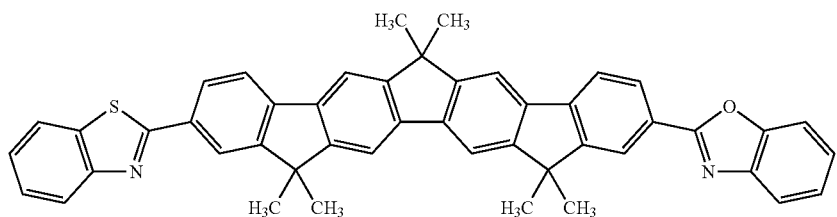
[46]
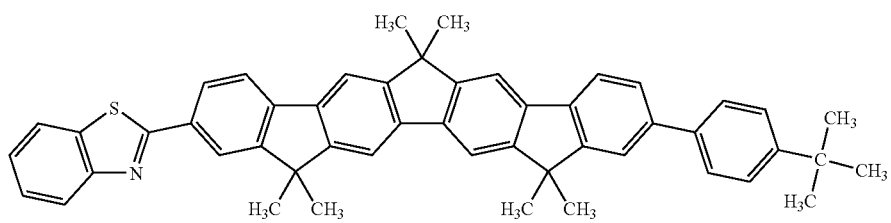
[47]
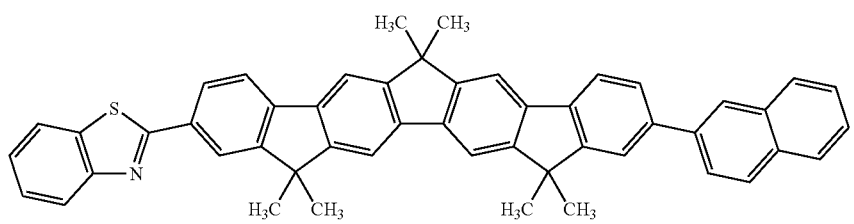
[48]
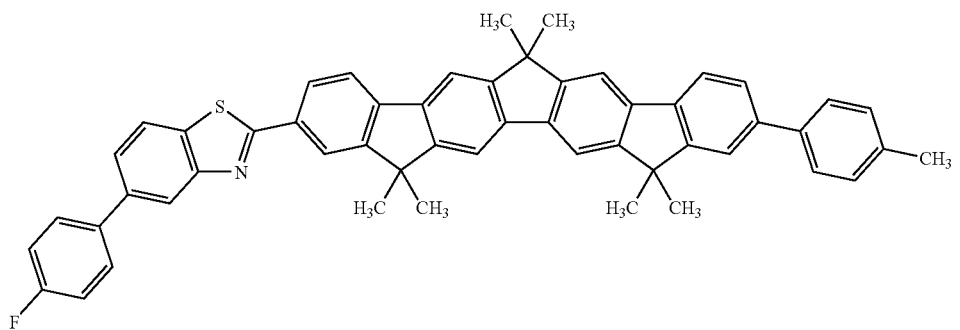
[49]
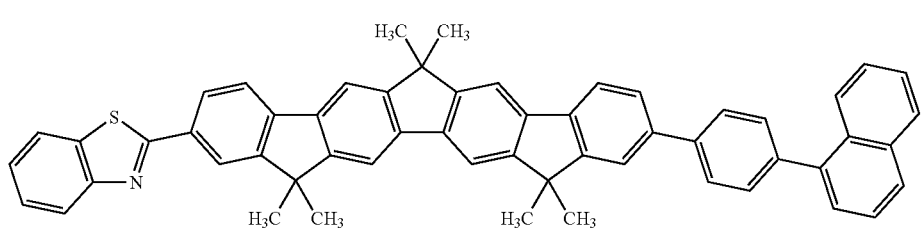
[50]
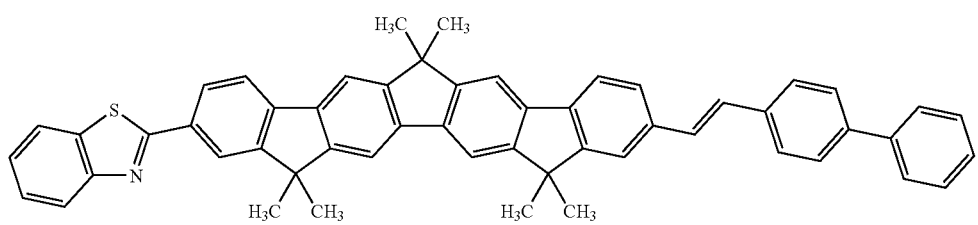
[51]

-continued
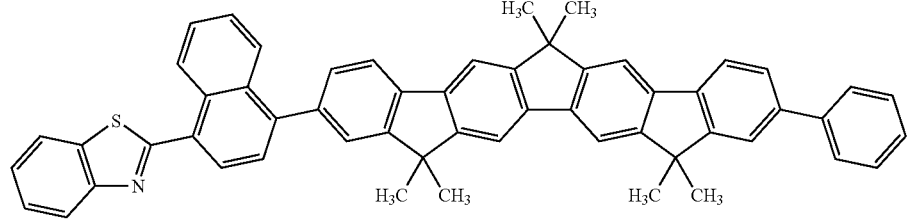
[52]
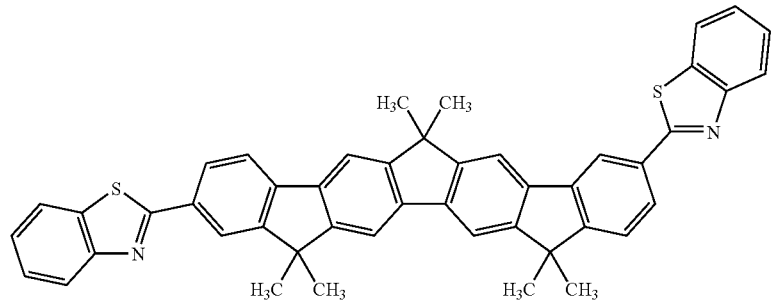
[53]
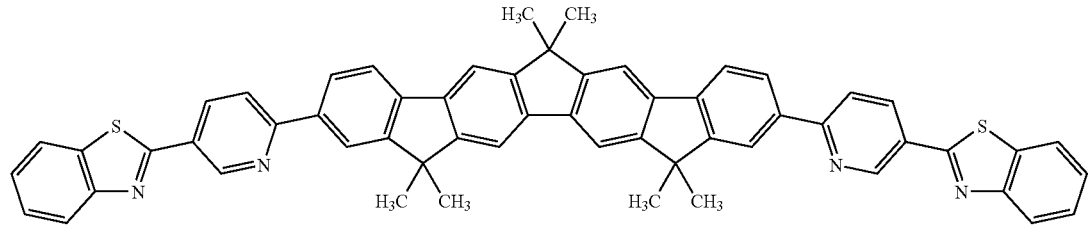
[54]
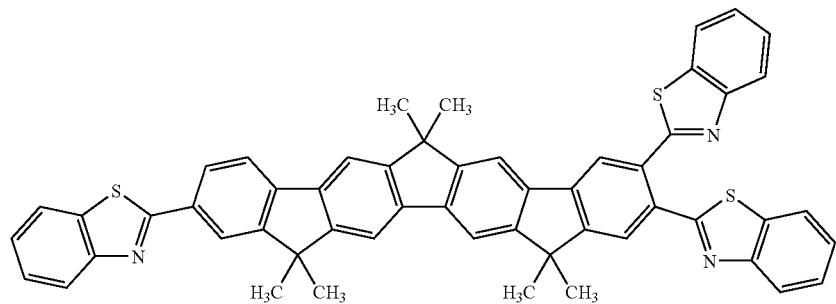
[55]
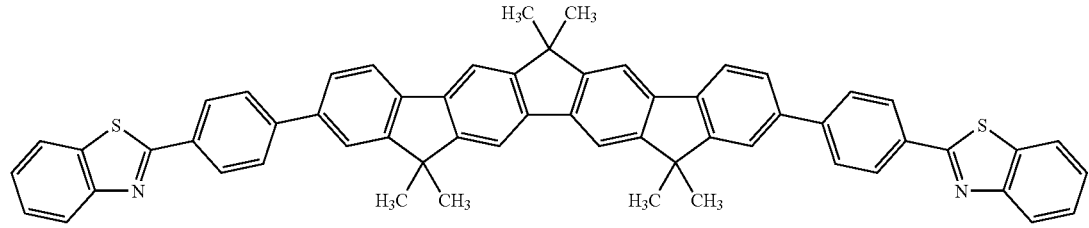
[56]
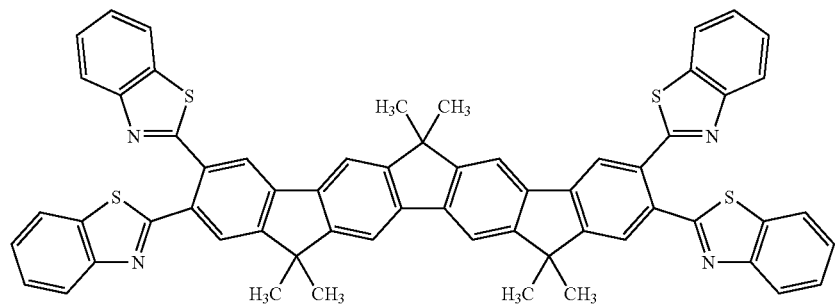
[57]

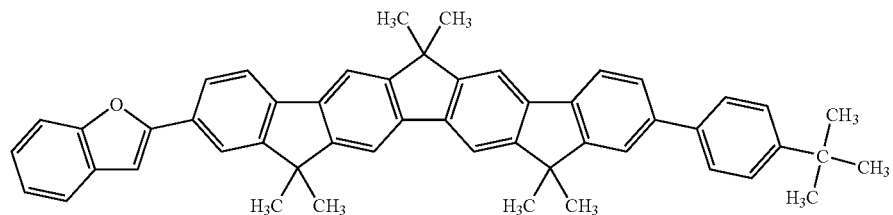
[58]
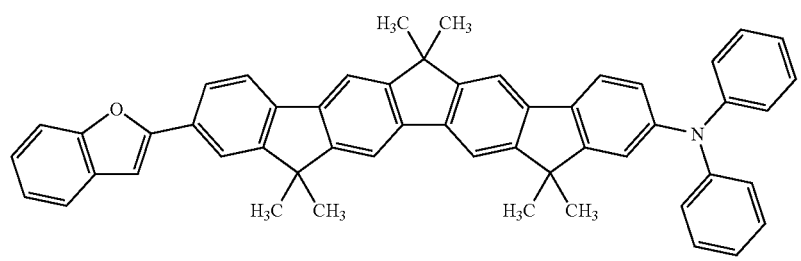
[59]
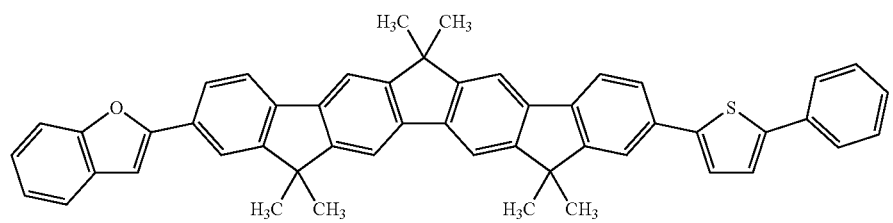
[60]
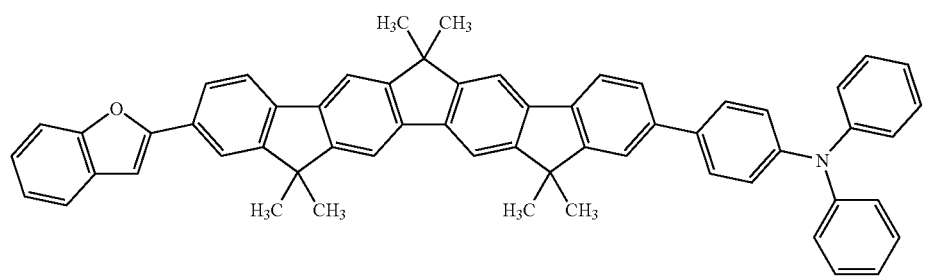
[61]
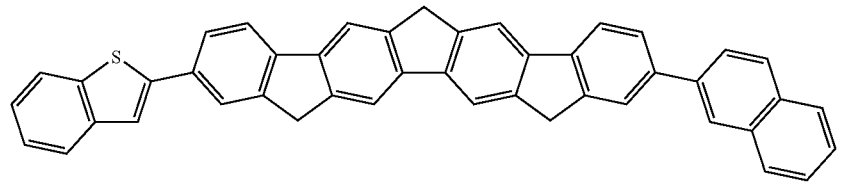
[62]
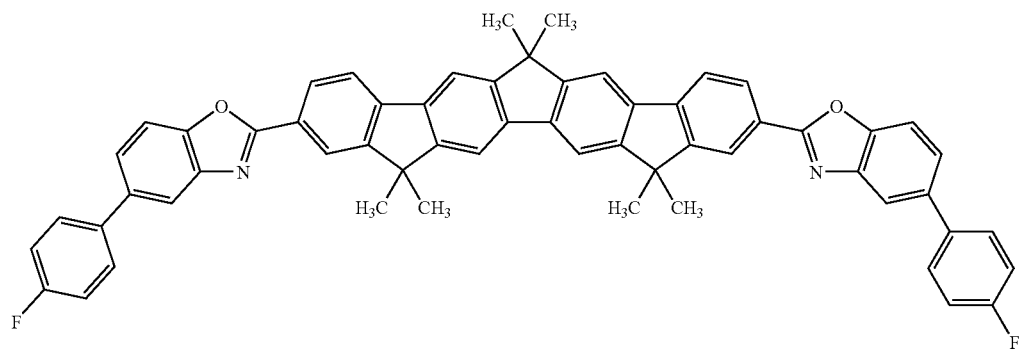
[63]

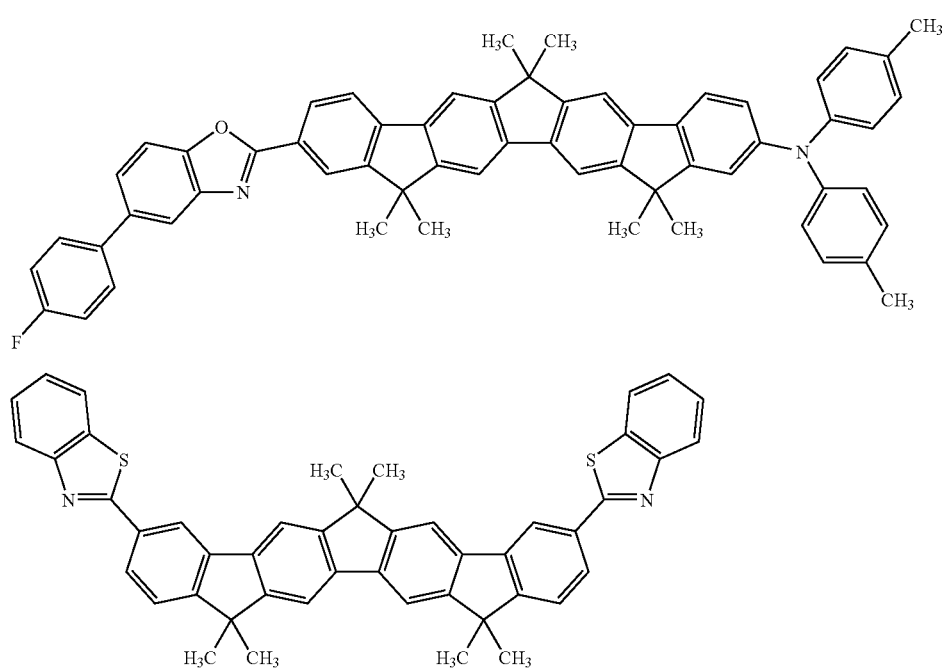

A publicly known method can be used for the synthesis of the fluorene compound represented by the general formula (1). Examples of a method of introducing an aryl group or a heteroaryl group to a fluorene skeleton include a method of using a coupling reaction of a halogenated fluorene derivative with an aryl derivative or a heteroaryl derivative in the presence of a palladium catalyst or a nickel catalyst. Examples of a method of introducing an azolyl group to a fluorene skeleton include, but are not limited to, a method of using a coupling reaction of a halogenated fluorene derivative with an azole derivative in the presence of a palladium catalyst and a method of using a condensation reaction of fluorene aldehyde or a fluorene carboxylic acid derivative with 2-aminophenol or 2-aminothiophenol.

Embodiments of the light emitting device in the present invention will be described in detail below by way of examples. According to exemplary embodiments, the light emitting device of the present invention comprises an anode, a cathode and an organic layer existing between the anode and the cathode, and the organic layer contains at least an emissive layer, and the emissive layer emits light by electric energy.

The organic layer may be of a structure composed only of an emissive layer, or has a layered structure of 1) hole transporting layer/emissive layer/electron transporting layer, 2) emissive layer/electron transporting layer or 3) hole transporting layer/emissive layer. Each of the aforementioned layers may be composed of a single layer or two or more layers. When a hole transporting layer and an electron transporting layer are each composed of two or more layers, layers in contact with an electrode are sometimes referred to as a hole injection layer and an electron injection layer, respectively. In the following description, a hole injection material and an electron injection material are included in the hole transporting material and the electron transporting material, respectively.

In the light emitting device of the present invention, the organic layer is preferably formed of the light emitting device material of embodiments of the present invention containing the fluorene compound represented by the general formula (1). The light emitting device material means a compound relating to light emission in a light emitting device and corresponds to either a material capable of emitting light itself or a material capable of assisting light emission. Specifically, the light emitting device material includes a hole transporting material, an emissive material, an electron transporting material and the like.

While the light emitting device material of the present invention may be used as a hole transporting material or an electron transporting material, it is suitably used as an emissive material because it has high light emitting performance. While the light emitting device material of the present invention is suitably used as a blue emissive material because it emits strong light in a blue region, it can also be used as a material for a green to red light emitting device and a white light emitting device. A white light emitting device can be obtained by laminating two or more materials different in color of emitted light. Specific examples thereof include a two-layer laminated white light emitting device of a light-blue emissive material and an orange emissive material and a three-layer laminated white light emitting device of a blue emissive material, a green emissive material, and a red emissive material. Since the light emitting device material of the present invention is suitably used as a blue emissive material, a white light emitting device can be obtained by forming a three-layer lamination with a green emissive material, such as 2,3,5,6-1H,4H-tetrahydro-9-(2'-benzothiazolyl)quinolidino[9,9a,1-gh]coumarin, and a red emissive material, such as 1,3,5,7-tetra(4-tert-butylphenyl)-8-phenyl-4,4-difluoro-4-bora-3a,4a-diaza-s-indacene, for example, as other emissive materials.

While the material of the anode is not particularly limited as long as it is a material capable of efficiently injecting holes into the organic layer, it is preferred to use a material having a comparatively large work function. Examples of the material of the anode include conductive metal oxides, such as tin oxide, indium oxide, zinc indium oxide and indium tin oxide (ITO); metals, such as gold, silver and chromium; inorganic conductive substances, such as copper iodide and copper sulfide; and conductive polymers, such as polythiophene, polypyrrole and polyaniline. These electrode materials may be used alone, or two or more materials may be laminated or mixed.

While the resistance of the anode is not particularly limited as long as a current required to perform light emission of the light emitting device can be supplied, low resistance is preferred in view of power consumption of the light emitting device. For example, while the anode can function as an electrode when the resistance is 300Ω/☐ or less, it is particularly preferred to use a product having a low resistance of 100Ω/☐ or less because it has become possible to supply an ITO substrate having about 10Ω/☐. The thickness of the anode can be optionally selected according to the resistance value, and it is usually from 100 to 300 nm in many cases.

In order to maintain the mechanical strength of the light emitting device, it is preferable to form the anode on a substrate. As the substrate, a substrate made of glass, such as soda glass or non-alkali glass, is suitably used. The thickness of the glass substrate may be a thickness enough for maintaining the mechanical strength and therefore a thickness of 0.5 mm or more is sufficient. Although non-alkali glass is preferred in that small number of ions are eluted from the glass, soda-lime glass with a $SiO_2$ barrier coat or the like is commercially available and can be used. Furthermore, if the anode stably functions, it is not necessary for the substrate to be made of glass and, for example, the anode may be formed on a plastic substrate. The method of forming an anode is not particularly limited and, for example, an electron beam method, a sputtering method and a chemical reaction method can be used.

The material used for the cathode is not particularly limited as long as it is a substance capable of efficiently injecting electrons into the organic layer, and examples thereof include platinum, gold, silver, copper, iron, tin, zinc, aluminum, indium, chromium, lithium, sodium, potassium, cesium, calcium and magnesium, or an alloy thereof. In order to improve device characteristics by increasing electron injection efficiency, lithium, sodium, potassium, cesium, calcium, magnesium or an alloy containing such low work function metals is effective. However, since these low work function metals are often unstable in the atmospheric air, one of preferable examples is a method comprising doping the organic layer with a trace amount (1 nm or less in thickness measured with a thickness meter for vacuum deposition) of lithium or magnesium to obtain a highly stable electrode. An inorganic salt such as lithium fluoride can also be used. One preferable example of procedures to be used for electrode protection is to laminate metals such as platinum, gold, silver, copper, iron, tin, aluminum and indium, alloys using such metals, inorganic substances such as silica, titania and silicon nitride, or organic polymer compounds such as polyvinyl alcohol, polyvinyl chloride and a hydrocarbon-based polymer compound. The method of forming a cathode is not particularly limited and, for example, resistance heating, electron beam, sputtering, ion plating and coating can be used.

The hole transporting layer is formed by a method of laminating or mixing one or two or more hole transporting materials or a method of using a mixture of a hole transporting material and a polymer binder. The hole transporting layer may be formed by adding an inorganic salt such as iron(III) chloride to the hole transporting material. The hole transporting material is not particularly limited as long as it is a compound that is capable of forming a thin film, injecting holes from the anode and transporting the holes. Preferred examples of the hole transporting materials include triphenylamine derivatives such as 4,4'-bis(N-(3-methylphenyl)-N-phenylamino)biphenyl, 4,4'-bis(N-(1-naphthyl)-N-phenylamino)biphenyl and 4,4',4"-tris(3-methylphenyl(phenyl)amino)triphenylamine; biscarbazole derivatives such as bis (N-allylcarbazole) and bis(N-alkylcarbazole); heterocyclic compounds such as pyrazoline derivatives, stilbene-based compounds, hydrazone-based compounds, benzofuran derivatives, thiophene derivatives, oxadiazole derivatives, phthalocyanine derivatives and porphyrin derivatives; and polymers such as polycarbonate having the above monomer in the side chain, styrene derivatives, polythiophene, polyaniline, polyfluorene, polyvinylcarbazole, and polysilane.

The emissive layer may have either a single layer or two or more layers and each layer may be made of a mixture of a host material and a dopant material or only a host material. Each of the host material and the dopant material may be used alone or in combination. The dopant material may be entirely or partially contained in the host material. The dopant material may be either laminated with the host material or dispersed in the host material. The amount of the dopant material is preferably 20% by weight or less, and more preferably 10% by weight or less based on the total amount of the host material and the dopant material because if it is too large, concentration quenching occurs. Regarding a doping method, the dopant material may be formed by a co-evaporation method with the host material, or evaporation may be performed after preliminarily mixing the host material and the dopant material. While the fluorene compound of the present invention may be used as a host material, it is suitably used as a dopant material because of its high fluorescence quantum yield.

The ionization potential of the fluorene compound of the present invention is not particularly limited, and it is preferably 4.5 eV or more and 7.0 eV or less, and more preferably 5.4 eV or more and 6.4 eV or less. An absolute value of the ionization potential may vary depending on the measuring method. The ionization potential referred to in the present invention is a value measured with an atmospheric air type UV photoelectron analyzer (AC-1, manufactured by RIKEN-KIKI CO., LTD.) by using a thin film formed in a thickness of 30 nm to 100 nm on an ITO glass substrate by vapor deposition.

As the dopant material, the fluorene compound represented by the general formula (1) may be used singly, or two or more fluorene compounds may be used in combination. The fluorene compound represented by the general formula (1) may also be mixed to use with one or more other dopant materials. Examples of the dopant material that may be mixed include compounds having an aryl ring, such as naphthalene, anthracene, phenanthrene, pyrene, triphenylene, perylene, fluorene and indene and derivatives thereof (for example, 2-(benzothiazol-2-yl)-9,10-diphenylanthracene, and 5,6,11,12-tetraphenylnaphthacene); compounds having a heteroaryl ring, such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthylidine, quinoxaline, pyrrolopyridine and thioxanthene, and derivatives thereof; distyrylbenzene derivatives; aminostyryl derivatives, such as 4,4'-bis(2-(4-diphenylaminophenyl)ethenyl)biphenyl and 4,4'-bis(N-(stilbene-4-yl)-N-phenylamino)stilbene; aromatic acetylene derivatives; tetraphenylbutadiene derivatives; stilbene derivatives; aldazine derivatives; pyrromethene derivatives; diketopyrrolo[3,4-c]pyrrole derivatives; cumarin derivatives, such as 2,3,5,6-1H,4H-tetrahydro-9-(2'-benzothiazolyl)quinolizino[9,9a,1-gh]cumarin; azole derivatives, such as imidazole, thiazole, thiadiazole, carbazole, oxazole, oxadiazole, and triazole, and metal complexes thereof; and aromatic amine derivatives typified by N,N'-diphenyl-N,N'-di(3-methylphenyl)-4,4'-diphenyl-1,1'-diamine.

While the host material to be contained in the emissive material is not particularly limited, and preferred examples of the host materials to be used include compounds having a fused aryl ring, such as anthracene and pyrene, and derivatives thereof; aromatic amine derivatives such as N,N'-dinaphthyl-N,N'-diphenyl-4,4'-diphenyl-1,1'-diamine; metal chelated oxynoid compounds including tris(8-quinolinate)aluminum(III); bisstyryl derivatives, such as distyrylbenzene derivatives; tetraphenylbutadiene derivatives; indene derivatives; cumarin derivatives; oxadiazole derivatives; pyrrolopyridine derivatives; perynone derivatives; cyclopentadiene derivatives; oxadiazole derivatives; carbazole derivatives; pyrrlopyrrole derivatives; and polymers such as polyphenylenevinylene derivatives, polyparaphenylene derivatives, polyfluorene derivatives, polyvinylcarbazole derivatives, and polythiophene derivatives. Particularly, use of a fused aromatic ring derivative having an electron-donating or neutral substituent as a host is preferred because the effect due to the high luminance efficiency that the fluorene compound of the present invention has is exerted more remarkably. Specifically, when using a compound selected from among anthracene compounds, pyrene compounds and distyrylbenzene derivatives as a host material, it is preferable because higher luminance efficiency is attained upon combination with the fluorene compound of the present invention.

The electron transporting layer is a layer that receives electrons injected from a cathode and further transports the electrons. The electron transporting layer is required to have a high electron injection efficiency and efficiently transport the injected electrons. Therefore, the electron transporting layer is preferably composed of a substance that has large electron affinity, large electron mobility and excellent stability and is less likely to generate, during production and use, impurities which will act as a trap. However, considering transportation balance between holes and electrons, if the electron transporting layer mainly plays a role of efficiently inhibiting holes from flowing toward the cathode from the anode without being recombined, there is exerted the same effect of improving luminance efficiency as that in a case where the electron transporting layer is made of a material having high electron transportation capability even if the electron transporting layer is made of a material having not so high electron transportation capability.

Examples of the electron transporting material to be used for the electron transporting layer include, but are not limited to, compounds having a fused aryl ring, such as naphthalene and anthracene, and derivatives thereof; styryl-based aromatic derivatives typified by 4,4'-bis(diphenylethenyl)biphenyl; perylene derivatives; perynone derivative; cumarin derivatives; naphthalimide derivatives; quinone derivatives, such as anthraquinone and diphenoquinone; phosphorus oxide derivatives; carbazole derivatives; indole derivatives; quinolinol complexes, such as tris(8-quinolinolate)aluminum (III); hydroxyazole complexes, such as hydroxyphenyloxazole complexes; azomethine complexes; tropolone metal complexes; and flavonol metal complexes. It is preferable to use, as an electron transporting material, a compound that is composed of elements selected from among carbon, hydrogen, nitrogen, oxygen, silicon, and phosphorus and has a heteroaryl ring structure containing an electron-accepting nitrogen because it is possible to reduce a driving voltage.

The electron-accepting nitrogen denotes a nitrogen atom which forms a multiple bond with an adjacent atom thereof. Since a nitrogen atom has a high electronegativity, the multiple bond has an electron-accepting property and a high electron transporting ability, and thus the driving voltage of a light emitting device can be decreased by using such a compound for the electron transporting layer. Therefore, a heteroaryl ring containing an electron-accepting nitrogen has high electron affinity. Examples of the heteroaryl ring containing an electron-accepting nitrogen include a pyridine ring, a pyrazine ring, a pyrimidine ring, a quinoline ring, a quinoxaline ring, a naphthylidine ring, a pyrimidopyrimidine ring, a benzoquinoline ring, a phenanthroline ring, an imidazole ring, an oxazole ring, an oxadiazole ring, a triazole ring, a thiazole ring, a thiadiazole ring, a benzooxazole ring, a benzothiazole ring, a benzimidazole ring and a phenanthroimidazole ring.

Preferred examples of the compounds having a heteroaryl ring structure include benzimidazole derivatives, benzoxazole derivatives, benzthiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives, such as bipyridine and terpyridine, quinoxaline derivatives, and naphthylidine derivatives. Among these compounds, there can be preferably used imidazole derivatives, such as tris(N-phenylbenzimidazol-2-yl)benzene; oxadiazole derivatives, such as 1,3-bis[(4-tert-butylphenyl)1,3,4-oxadiazolyl]phenylene; triazole derivatives, such as N-naphthyl-2,5-diphenyl-1,3,4-triazole; phenanthroline derivatives, such as bathocuproine and 1,3-bis(1,10-phenanthrolin-9-yl)benzene; benzoquinoline derivatives, such as 2,2'-bis(benzo[h]quinolin-2-yl)-9,9'-spirobifluorene; bipyridine derivatives, such as 2,5-bis(6'-(2',2"-bipyridyl))-1,1-dimethyl-3,4-diphenylsilole; terpyridine derivatives, such as 1,3-bis(4'-(2,2':6'2"-terpyridinyl))benzene; and naphthylidine derivatives, such as bis(1-naphthyl)-4-(1,8-naphthylidin-2-yl)phenylphosphine oxide in view of electron transporting ability. Furthermore, phenanthroline dimers, such as 1,3-bis(1,10-phenanthrolin-9-yl)benzene, 2,7-bis(1,10-phenanthrolin-9-yl)naphthalene and 1,3-bis(2-phenyl-1,10-phenanthrolin-9-yl)benzene; and bipyridine dimers, such as 2,5-bis(6'-(2',2"-bipyridyl))-1,1-dimethyl-3,4-diphenylsilole are particularly preferable examples because a remarkably high effect of improving luminance efficiency is exerted when used in combination with an emissive layer containing the fluorene compound represented by the general formula (1).

While the aforementioned electron transporting materials may be used singly, two or more of the electron transporting materials may be mixed to be used, or the electron transporting materials each may be mixed with one or more other electron transporting materials to be used. Moreover, the electron transporting materials each may be mixed with a metal, such as alkali metals and alkali earth metals to be used. While the ionization potential of the electron transporting layer is not particularly limited, it is preferably 5.8 eV or more and 8.0 eV or less, and more preferably 6.0 eV or more and 7.5 eV or less.

Examples of the method of forming each layer constituting the light emitting device include, but are not limited to, a resistance heating evaporation method, an electron beam evaporation method, a sputtering method, a molecular stacking method, a coating method, an ink-jetting method, a printing method, a laser induced thermal transfer method and the like. In view of device characteristics, a resistance heating evaporation method or an electron beam evaporation method is usually preferred.

While the thickness of each layer depends on the resistance value of an emissive substance and cannot be limited, it is selected from between 1 nm and 1,000 nm. The thickness of each of the emissive layer, the electron transporting layer and the hole transporting layer is preferably 1 nm or more and 200 nm or less, and more preferably 5 nm or more and 100 nm or less.

The light emitting device of the present invention has a function of converting electric energy into light. While a DC current is mainly used as the electric energy, a pulse current or an AC current can also be used. The values of the electric current and the voltage are not particularly limited. However, taking into consideration the power consumption and the life of the device, the values are preferably selected so that maximum luminance can be obtained at an energy as low as possible.

The light emitting device of the present invention can be used suitably as matrix and/or segment system displays.

In the matrix system, pixels for display are two-dimensionally disposed in lattice or mosaic, and characters and images are displayed by sets of pixels. The shape and size of the pixels are determined according to the intended application. In the case of image and character display by personal computers, monitors and televisions, there are normally used square-shaped pixels with up to 300 μm sides, and in the case of large-size displays, such as display panels, there are normally used pixels with sides of mm order. Pixels in the same color are merely arrayed in the case of monochrome display, while pixels in red, green and blue are arrayed for indicating in the case of color display. In the color display, the arrangement system typically includes a delta type system and a stripe type system. A matrix driving method may be either passive matrix driving or active matrix driving. While the passive matrix driving is simple in the structure of a light emitting device, active matrix driving is sometimes more advantageous when taking operation characteristics into consideration. The driving method is properly used according to the intended application.

The segment system is a system wherein a pattern is formed so as to display prescribed information and the range determined by the arrangement of the pattern is allowed to emit light. Examples thereof include time and temperature displays in digital watches and thermometers, operation state displays in audio instruments and microwave cookers, and vehicle panel displays. The matrix display and the segment display may be present together in the same panel.

The light emitting device of the present invention can also be preferably employed as backlight. The backlight is mainly used for the purpose of improving visibility of a display device which itself emits no light, and it is used in liquid crystal display devices, watches, audio equipments, automobile panels, display plates, and signs. The light emitting device of the present invention is preferably used as the backlight of a liquid crystal display device, particularly a personal computer in which the thickness reduction is studied. The light emitting device of the present invention can provide backlight that is smaller in thickness and weight than conventional products.

EXAMPLES

Embodiments of the present invention will be described below by way of Examples, but the present invention is not limited to the following Examples. Numbers of compounds in the following Examples mean numbers of compounds described in the above chemical formulas. A method for evaluation of structural analysis will be shown below.

$^1$H-NMR was measured by Superconductive FTNMR EX-270 (manufactured by JEOL Ltd.) using a deuterated chloroform solution.

HPLC was measured by a 0.1 g/L chloroform solution using a high performance liquid chromatograph LC-10 (manufactured by Shimadzu Corporation). As an eluent of a column, a mixed solution of an aqueous 0.1% phosphoric acid solution and acetonitrile was used.

Example 1

Synthesis of Compound [10]

(1-1) Synthesis of Intermediate A

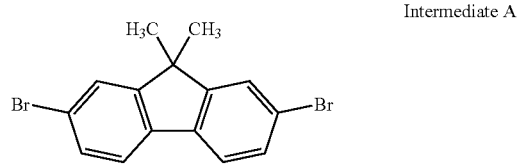

Intermediate A

Under a nitrogen flow, 25.0 g of 2,7-dibromofluorene, 22.6 g of potassium tert-butoxide, and 300 mL of dimethyl sulfoxide were charged into a 1-L four-necked flask and the reaction system was cooled to 5° C. Subsequently, 32.8 g of methyl iodide was dropped slowly, followed by stirring at room temperature for 2 hours. After the completion of reaction, 500 mL of water was added, followed by extraction with 300 mL of dichloromethane. The organic layer was washed with 200 mL of water, dried over magnesium sulfate, and then the solvent was removed with a rotary evaporator. The resulting crude reaction product was washed twice with 200 mL of methanol, and the precipitated crystals were collected by filtration. After vacuum drying, 23.6 g of an intended intermediate A (yellowish white crystal; yield 87%) was obtained.

(1-2) Synthesis of Intermediate B

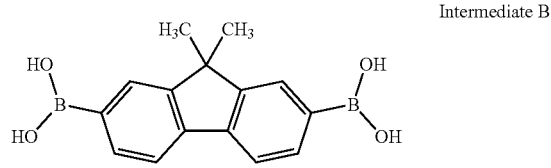

Intermediate B

Under a nitrogen flow, 20.6 g of the intermediate A and 350 mL of tetrahydrofuran were charged into a 1-L four-necked flask and the reaction system was cooled to −70° C. Subsequently, 110 mL of n-butyllithium (1.6 M hexane solution) was dropped slowly, followed by stirring at −10° C. for 1 hour. Then, the reaction system was cooled to −50° C. and 41 mL of boronic acid triisopropoxide was dropped slowly, followed by stirring at room temperature for 2 hours. After the completion of reaction, 300 mL of diluted hydrochloric acid was added and followed by stirring at room temperature for 2 hours, and then the organic layer was extracted. The extracted organic layer was washed with 300 mL of saturated brine, dried over magnesium sulfate, and then the solvent was removed with a rotary evaporator. The resulting crude reaction product was washed by stirring in a mixed solution of 100 mL of ethyl acetate/200 mL of n-hexane, and the precipitated crystals were collected by filtration. After vacuum drying, 11.0 g of an intended intermediate B (white crystal; yield 67%) was obtained.

(1-3) Synthesis of Intermediate C

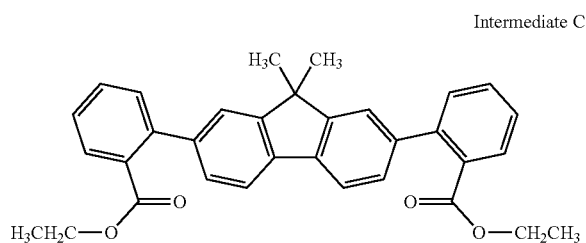

Intermediate C

Under a nitrogen flow, 11.0 g of the intermediate B, 22.3 g of ethyl 2-bromobenzoate, 4.5 g of tetrakistriphenylphosphine palladium(0), 160 mL of toluene, 100 mL of ethanol, and 24.8 g of sodium carbonate/120 mL of water were charged into a 1-L four-necked flask, followed by heating under reflux for 8 hours. After the reaction solution was cooled to room temperature, the organic layer was extracted and washed twice with 200 mL of saturated brine, dried over magnesium sulfate, and then the solvent was removed with a rotary evaporator. The resulting crude reaction product was washed by stirring in 200 mL of methanol, and the precipitated crystals were collected by filtration. After vacuum drying, 16.3 g of an intended intermediate C (yellowish white crystal; yield 85%) was obtained.

(1-4) Synthesis of Intermediate D

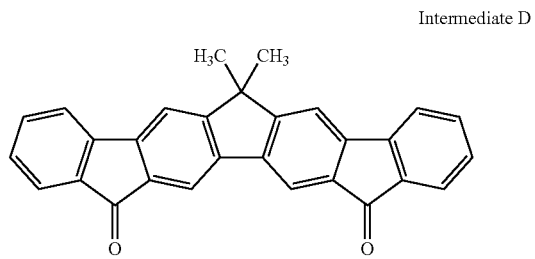

Intermediate D

Under a nitrogen flow, 16.3 g of the intermediate C and 200 mL of polyphosphoric acid were charged into a 1-L four-necked flask, followed by heating at 120° C. for 10 hours. After the completion of reaction, the resulting mixture was added to 1500 mL of water and the precipitated powder was collected by filtration. The resulting crude reaction product was purified by silica gel column chromatography and then vacuum dried to obtain 7.5 g of an intended intermediate D (reddish orange crystal; yield 56%).

(1-5) Synthesis of Intermediate E

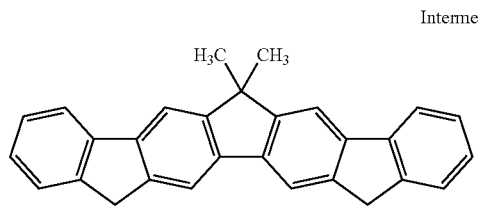

Intermediate E

Under a nitrogen flow, 7.0 g of the intermediate D, 4.4 g of hydrazine monohydrate, 3.5 g of potassium hydroxide, and 120 mL of diethylene glycol were charged into a 500-mL four-necked flask, followed by heating at 180° C. for 2 hours. After the reaction solution was cooled to room temperature, 300 mL of water was added and the precipitated powder was collected by filtration. The resulting crude reaction product was washed by stirring in 100 mL of methanol and then vacuum dried to obtain 3.4 g of an intended intermediate E (orange crystal; yield 52%).

(1-6) Synthesis of Intermediate F

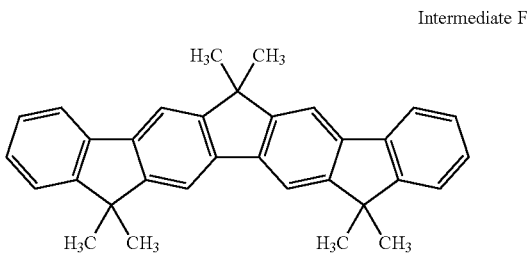

Intermediate F

Under a nitrogen flow, 3.4 g of the intermediate E, 6.5 g of potassium tert-butoxide, and 130 mL of dimethyl sulfoxide were charged into a 500-mL four-necked flask and the reaction system was cooled to 5° C. Subsequently, 8.3 g of methyl iodide was dropped slowly, followed by stirring at room temperature for 2 hours. After the completion of reaction, 250 mL of water was added, followed by extraction with 200 mL of dichloromethane. The organic layer was washed with 100 mL of water, dried over magnesium sulfate, and then the solvent was removed with a rotary evaporator. The resulting crude reaction product was purified by silica gel column chromatography and then vacuum dried to obtain 2.9 g of an intended intermediate F (white crystal; yield 74%).

(1-7) Synthesis of Intermediate G

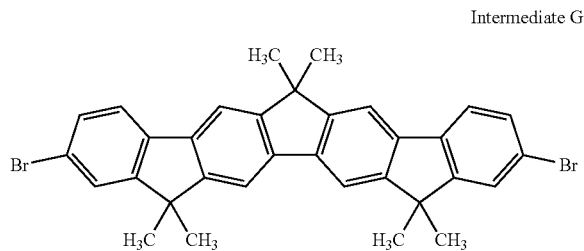

Intermediate G

Under a nitrogen flow, 2.9 g of the intermediate F and 50 mL of chloroform were charged into a 300-mL three-necked flask. Subsequently, 2.4 g of bromine was dropped slowly, followed by stirring at room temperature for 6 hours. After the completion of reaction, 200 mL of an aqueous sodium thiosulfate solution was added to the reaction solution and then the organic layer was extracted. The organic layer was dried over sodium sulfate, and then the solvent was removed with a rotary evaporator. The resulting crude reaction product was washed by stirring in 50 mL of methanol and then vacuum dried to obtain 3.9 g of an intended intermediate G (white crystal; yield 98%).

(1-8) Synthesis of Compound [10]

Under a nitrogen flow, 0.30 g of the intermediate G, 0.25 g of 2-benzofuranboronic acid, 0.06 g of tetrakistriphenylphosphine palladium(0), 4 mL of toluene, 2 mL of ethanol, and 0.33 g of sodium carbonate/2 mL of water were charged into a 50-mL two-necked flask, followed by heating under reflux for 8 hours. After the reaction solution was cooled to room temperature, the organic layer was extracted and washed twice with 10 mL of saturated brine, dried over magnesium sulfate, and then the solvent was removed with a rotary evaporator. The resulting crude reaction product was purified by silica gel column chromatography and then vacuum dried to obtain 0.20 g of a yellow powder (yield 60%). $^1$H-NMR analytical results of the resultant powder are as follows and revealed that the yellow powder obtained above was compound [10].

$^1$H NMR (CDCl$_3$ (d=ppm)): 1.66 (s, 6H), 1.68 (s, 12H), 7.25-7.60 (m, 10H), 7.75-8.25 (m, 10H).

This compound [10] was used as a light emitting device material after being subjected to sublimation purification under a pressure of $1\times10^{-3}$ Pa at about 300° C. using an oil diffusion pump. HPLC purity (area % at a measuring wavelength of 254 nm) was 99.2% before sublimation purification and was 99.3% after sublimation purification.

Example 2

Synthesis of Compound [43]

Under a nitrogen flow, 0.30 g of the intermediate G, 0.28 g of benzothiazole, 0.67 g of cesium carbonate, 40 mg of copper iodide, 11 mg of triphenylphosphine, 5 mg of palladium acetate, and 10 mL of degassed dimethylformamide were charged into a 50-mL two-necked flask, followed by heating under stirring at 140° C. for 4 hours. After cooling the reaction solution to room temperature, 50 mL of water was added, followed by extraction with 100 mL of dichloromethane. The organic layer was washed twice with 50 mL of water, dried over magnesium sulfate, and then the solvent was removed with a rotary evaporator. The resulting crude reaction product was purified by silica gel column chromatography and then vacuum dried to obtain 0.15 g of a yellow powder (yield 43%). $^1$H-NMR analytical results of the resultant powder are as follows and revealed that the yellow powder obtained above was compound [43].

$^1$H-NMR (CDCl$_3$ (d=ppm)): 1.66 (s, 6H), 1.68 (s, 12H), 7.35-7.56 (m, 4H), 7.83-7.96 (m, 8H), 8.09-8.15 (m, 4H), 8.23 (s, 2H).

This compound [43] was used as a light emitting device material after being subjected to sublimation purification under a pressure of $1\times10^{-3}$ Pa at about 310° C. using an oil diffusion pump. HPLC purity (area % at a measuring wavelength of 254 nm) was 99.5% before sublimation purification and was 99.6% after sublimation purification.

Example 3

Synthesis of Compound [47]

(3-1) Synthesis of Intermediate H

Under a nitrogen flow, 0.60 g of the intermediate G, 0.32 g of 4-tert-butylphenylboronic acid, 0.75 g of tripotassium phosphate, 76 mg of tetrabutylammonium bromide, 5 mg of palladium acetate, and 12 mL of degassed dimethylformamide were charged into a 100-mL three-necked flask, followed by heating under stirring at 120° C. for 3 hours. After the solution was cooled to room temperature, 50 mL of water was added and the precipitated powder was collected by filtration. The resulting crude reaction product was purified by silica gel column chromatography and then vacuum dried to obtain 0.58 g of an intended intermediate H (white crystal; yield 89%).

(3-2) Synthesis of Compound [47]

Under a nitrogen flow, 0.58 g of the intermediate H, 0.25 g of benzothiazole, 0.61 g of cesium carbonate, 36 mg of copper iodide, 10 mg of triphenylphosphine, 5 mg of palladium acetate, and 10 mL of degassed dimethylformamide were charged into a 100-mL two-necked flask, followed by heating under stirring at 140° C. for 5 hours. After cooling the reaction solution to room temperature, 30 mL of water was added, followed by extraction with 100 mL of dichloromethane. The organic layer was washed twice with 50 mL of water, dried over magnesium sulfate, and then the solvent was removed with a rotary evaporator. The resulting crude reaction product was purified by silica gel column chromatography and then vacuum dried to obtain 0.16 g of a yellow powder (yield 25%). $^1$H-NMR analytical results of the resultant powder are as follows and revealed that the yellow powder obtained above was compound [47].

$^1$H-NMR (CDCl$_3$ (d=ppm)): 1.38 (s, 9H), 1.39 (s, 6H), 1.61 (s, 6H), 1.67 (s, 6H), 7.45-7.90 (m, 16H), 8.08 (d, 1H), 8.25 (d, 1H).

This compound [47] was used as a light emitting device material after being subjected to sublimation purification under a pressure of $1\times10^{-3}$ Pa at about 300° C. using an oil diffusion pump. HPLC purity (area % at a measuring wavelength of 254 nm) was 99.4% before sublimation purification and was 99.5% after sublimation purification.

Example 4

Synthesis of Compound [9]

Under a nitrogen flow, 1.00 g of the intermediate G, 4.90 g of 3-phenyl-2-benzofuranboronic acid, 0.40 g of tetrakistriphenylphosphine palladium(0), 12 mL of toluene, 7.5 mL of ethanol, and 2.18 g of sodium carbonate/12 mL of water were charged into a 100-mL three-necked flask, followed by heating under reflux for 6 hours. After the reaction solution was cooled to room temperature, the organic layer was extracted and washed twice with 10 mL of saturated brine, dried over magnesium sulfate, and then the solvent was removed with a rotary evaporator. The resulting crude reac- Intermediate H

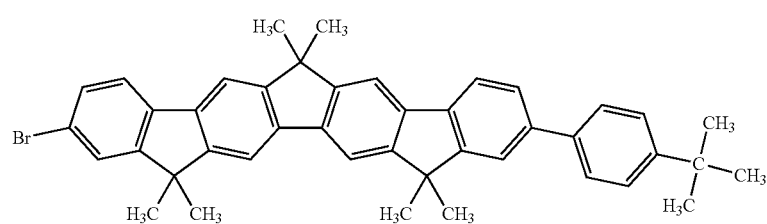

tion product was purified by silica gel column chromatography and then vacuum dried to obtain 0.32 g of a yellow powder (yield 23%). $^1$H-NMR analytical results of the resultant powder are as follows and revealed that the yellow powder obtained above was compound [9].

$^1$H-NMR (CDCl$_3$ (d=ppm)): 1.66 (s, 6H), 1.68 (s, 12H), 7.25-7.63 (m, 18H), 7.75-8.25 (m, 10H).

This compound [9] was used as a light emitting device material after being subjected to sublimation purification under a pressure of 1×10$^{-3}$ Pa at about 300° C. using an oil diffusion pump. HPLC purity (area % at a measuring wavelength of 254 nm) was 99.3% before sublimation purification and was 99.6% after sublimation purification.

Example 5

Synthesis of Compound [63]

Under a nitrogen flow, 1.53 g of the intermediate G, 0.56 g of 5-(4-fluorophenyl)benzoxazole, 0.86 g of cesium carbonate, 0.15 g of copper iodide, 42 mg of triphenylphosphine, 18 mg of palladium acetate, and 26 mL of degassed dimethylformamide were charged into a 100-mL three-necked flask, followed by heating under stirring at 140° C. for 2 hours. After cooling the reaction solution to room temperature, 50 mL of water was added, followed by extraction with 100 mL of dichloromethane. The organic layer was washed twice with 50 mL of water, dried over magnesium sulfate, and then the solvent was removed with a rotary evaporator. The resulting crude reaction product was purified by silica gel column chromatography and then vacuum dried to obtain 0.55 g of a yellow powder (yield 29%). $^1$H-NMR analytical results of the resultant powder are as follows and revealed that the yellow powder obtained above was compound [63].

$^1$H-NMR (CDCl$_3$ (d=ppm)): 1.66 (s, 6H), 1.68 (s, 12H), 7.03-7.48 (m, 14H), 7.63-8.01 (m, 10H).

This compound [63] was used as a light emitting device material after being subjected to sublimation purification under a pressure of 1×10$^{-3}$ Pa at about 350° C. using an oil diffusion pump. HPLC purity (area % at a measuring wavelength of 254 nm) was 99.5% before sublimation purification and was 99.9% after sublimation purification.

Example 6

A light emitting device using the compound [10] was produced in the following manner. On a glass substrate measuring 30×40 mm (manufactured by Asahi Glass Co., Ltd., 15Ω/☐, electron beam evaporated product), an ITO conductive film measuring 150 nm in thickness and 30×13 mm in size was formed in the center of the glass substrate to obtain an anode. The substrate with the anode formed thereon was subjected to ultrasonic washing for 15 minutes using "SEMI-COCLEAN (Registered trademark) 56" (manufactured by Furuuchi Chemical Corporation), followed by washing with ultra-pure water. The substrate was subjected to ultrasonic washing for 15 minutes using isopropyl alcohol, immersed in hot methanol for 15 minutes and then dried. Immediately before production of the device, this substrate was subjected to UV/ozone treatment for one hour and placed in a vacuum vapor-deposition equipment, and then the equipment was evacuated until the degree of vacuum in the equipment reached 5×10$^{-5}$ Pa or less.

On the ITO film of the substrate, a 10 nm thick layer of copper phthalocyanine as a hole injection material was formed first, and a 50 nm thick layer of 4,4'-bis(N-(1-naphthyl)-N-phenylamino)biphenyl as a hole transporting material was formed using a resistance heating method. Using H-1 represented by the following formula as a host material and the compound [10] as a dopant material, a 35 nm thick layer of an emissive material having a doping concentration of 2% was laminated. Then, a 20 nm thick layer of E-1 represented by the following formula as an electron transporting material was formed. On the organic layer thus formed, a 0.5 nm thick layer of lithium fluoride was formed and then a 1,000 nm thick layer of aluminum was formed to obtain a cathode, and thus a device measuring 5×5 mm was produced. The film thickness as referred to herein is the value displayed by a quartz crystal oscillator type film thickness monitor. This light emitting device was subjected to DC driving at 10 mA/cm$^2$. As a result, light was emitted at a high luminance efficiency of 2.61 lm/W and blue light having a high chromatic purity in terms of C.I.E chromaticity coordinate of (0.15, 0.12) was emitted. This light emitting device was subjected to continuous DC driving at 10 mA/cm$^2$. As a result, a luminance half-decay lifetime was 2,600 hours.

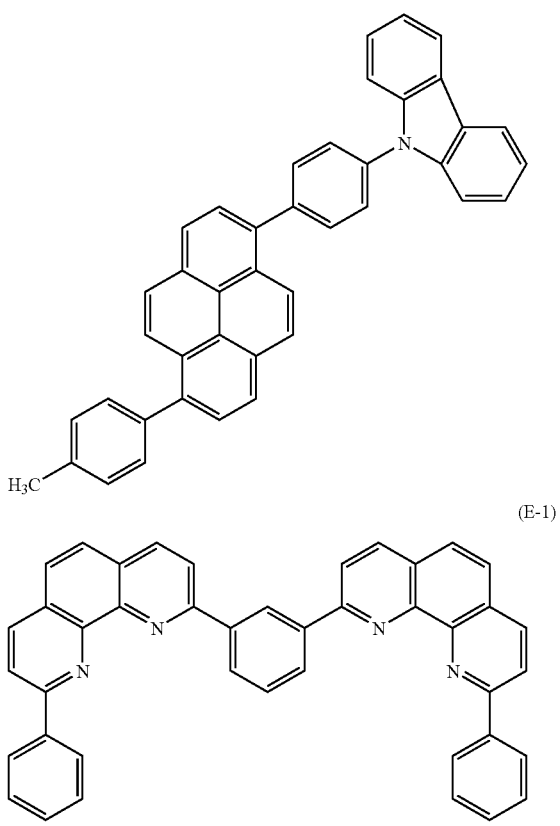

Examples 7 to 16, Comparative Examples 1 to 4

Each of light emitting devices was produced in the same manner as in Example 6 except for using materials described in Table 1 as dopant materials. The results of each Examples and Comparative Examples were shown in Table 1.

TABLE 1

|  | Emissive Layer | | Electron Transporting Layer | Color of Light Emission | Luminance Efficiency (lm/W) | C.I.E (x, y) | Luminance half-decay lifetime (h) |
|---|---|---|---|---|---|---|---|
|  | Host Material | Dopant Material | | | | | |
| Example 6 | H-1 | Compound [10] | E-1 | Blue | 2.6 | (0.15, 0.12) | 2600 |
| Example 7 | H-1 | Compound [43] | E-1 | Blue | 3.2 | (0.15, 0.10) | 3900 |
| Example 8 | H-1 | Compound [47] | E-1 | Blue | 2.8 | (0.15, 0.14) | 3300 |
| Example 9 | H-1 | Compound [62] | E-1 | Blue | 2.0 | (0.14, 0.09) | 2000 |
| Example 10 | H-1 | Compound [25] | E-1 | Blue | 2.6 | (0.15, 0.11) | 2100 |
| Example 11 | H-1 | Compound [14] | E-1 | Blue | 2.1 | (0.15, 0.15) | 2400 |
| Example 12 | H-1 | Compound [9] | E-1 | Blue | 2.5 | (0.15, 0.10) | 2500 |
| Example 13 | H-1 | Compound [58] | E-1 | Blue | 2.7 | (0.15, 0.10) | 2100 |
| Example 14 | H-1 | Compound [16] | E-1 | Blue | 2.8 | (0.15, 0.11) | 2200 |
| Example 15 | H-1 | Compound [63] | E-1 | Blue | 3.0 | (0.15, 0.12) | 3800 |
| Example 16 | H-1 | Compound [65] | E-1 | Blue | 2.1 | (0.15, 0.14) | 2000 |
| Comparative Example 1 | H-1 | D-1 | E-1 | Blue | 1.4 | (0.15, 0.18) | 400 |
| Comparative Example 2 | H-1 | D-2 | E-1 | Light Blue | 2.9 | (0.18, 0.38) | 300 |
| Comparative Example 3 | H-1 | D-3 | E-1 | Blue | 1.1 | 0.15, 0.17) | 600 |
| Comparative Example 4 | H-1 | D-4 | E-1 | Light Blue | 2.4 | (0.17, 0.27) | 200 |

D-1 to D-4 in Table 1 are compounds represented by the following formulae:

(D-1)

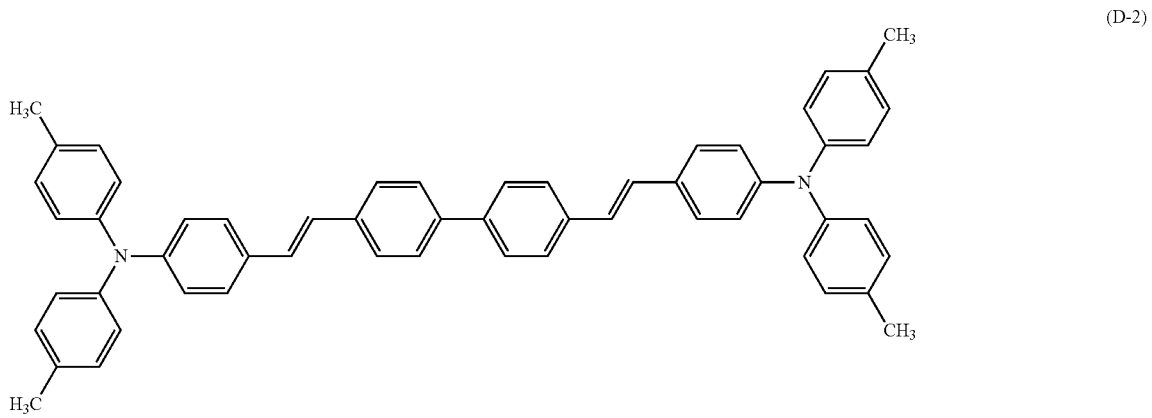

(D-2)

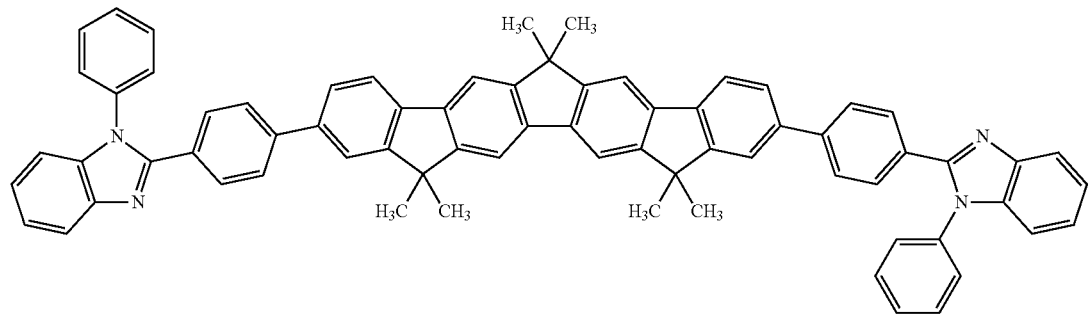

(D-3)

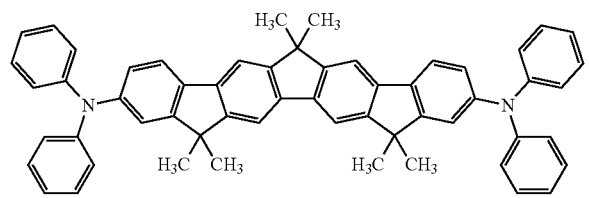

(D-4)

Examples 17 to 19

Each of the light emitting devices was produced in the same manner as in Example 6 except for using materials described in Table 2 as host materials. The results of each Examples were shown in Table 2.

TABLE 2

| | Emissive Layer | | Electron Transporting | Color of Light | Luminance Efficiency | C.I.E | Luminance half-decay lifetime |
|---|---|---|---|---|---|---|---|
| | Host Material | Dopant Material | Layer | Emission | (lm/W) | (x, y) | (h) |
| Example 17 | H-2 | Compound [43] | E-1 | Blue | 3.6 | (0.15, 0.16) | 2900 |
| Example 18 | H-3 | Compound [43] | E-1 | Blue | 2.8 | (0.15, 0.11) | 3400 |
| Example 19 | H-4 | Compound [43] | E-1 | Blue | 2.6 | (0.15, 0.12) | 3500 |

H-2 to H-4 in Table 2 are compounds represented by the following formulae:

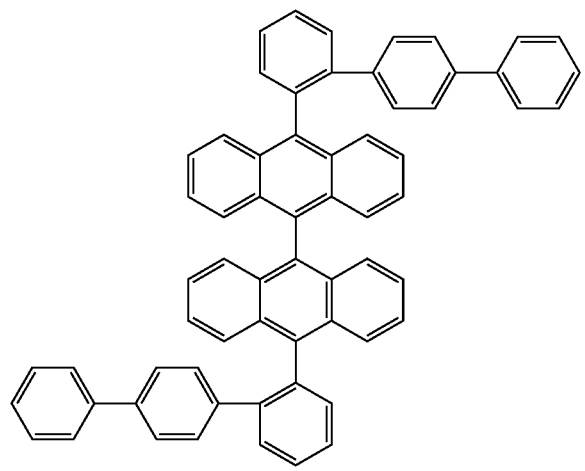

(H-2)

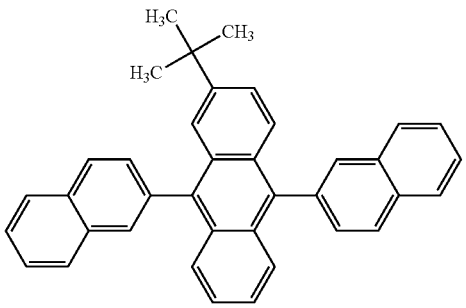

(H-3)

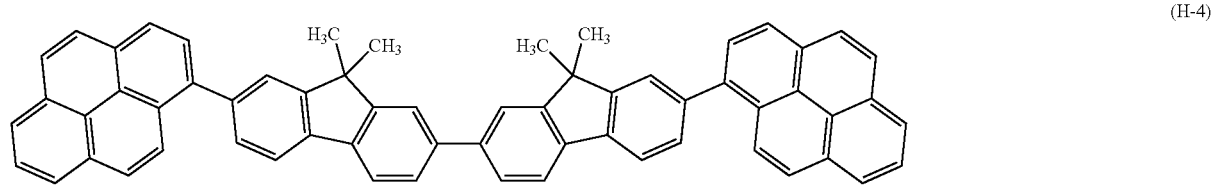

(H-4)

Examples 20- to 23

Each of the light emitting devices was produced in the same manner as in Example 6 except for using materials given in Table 3 as electron transporting materials. The results of each Examples were shown in Table 3.

TABLE 3

|  | Emissive Layer | | Electron Transporting Layer | Color of Light Emission | Luminance Efficiency (lm/W) | C.I.E (x, y) | Luminance half-decay lifetime (h) |
| --- | --- | --- | --- | --- | --- | --- | --- |
|  | Host Material | Dopant Material | | | | | |
| Example 20 | H-1 | Compound [43] | E-2 | Blue | 1.7 | (0.15, 0.15) | 2800 |
| Example 21 | H-1 | Compound [43] | E-3 | Blue | 3.1 | (0.15, 0.10) | 3700 |
| Example 22 | H-1 | Compound [43] | E-4 | Blue | 3.0 | (0.15, 0.11) | 3600 |
| Example 23 | H-1 | Compound [43] | E-5 | Blue | 1.9 | (0.15, 0.14) | 2900 |

E-2 to E-5 in Table 4 are compounds represented by the following formulae:

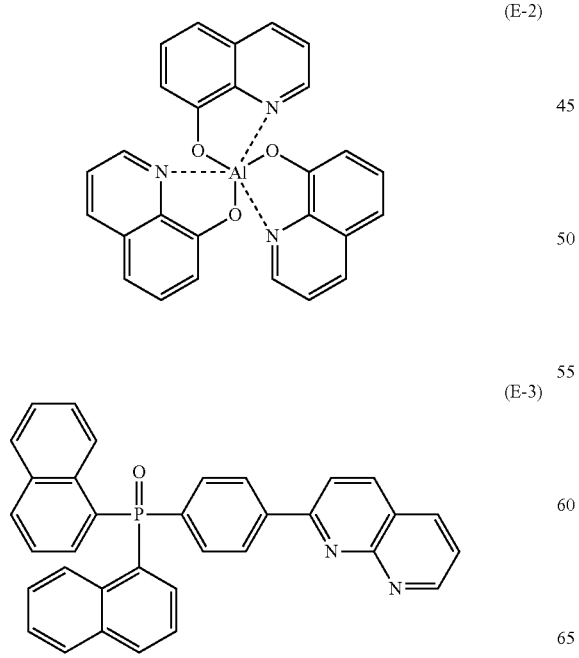

(E-2)

(E-3)

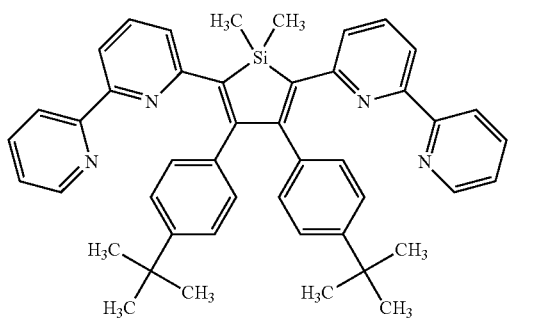

(E-4)

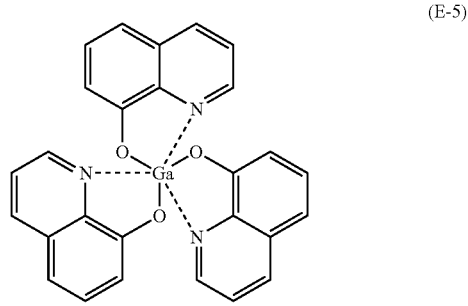

(E-5)

Example 24

On a glass substrate measuring 30×40 mm (manufactured by Asahi Glass Co., Ltd., 15Ω/□, electron beam evaporated product), an ITO conductive film measuring 150 nm in thickness and 30×13 mm in size was formed in the center of the glass substrate to obtain an anode. The substrate with the anode formed thereon was subjected to ultrasonic washing for 15 minutes using "SMICOCLEAN (Registered trademark) 56" (manufactured by Furuuchi Chemical Corporation), followed by washing with ultra-pure water. The substrate was subjected to ultrasonic washing for 15 minutes using isopropyl alcohol, immersed in hot methanol for 15 minutes and then dried. Immediately before production of the device, this substrate was subjected to UV/ozone treatment for one hour and placed in a vacuum vapor-deposition equipment, and then the equipment was evacuated until the degree of vacuum inside reached $5 \times 10^{-4}$ Pa or less.

On the ITO film of the substrate, a 150 nm thick layer of 4,4'-bis(N-(m-tolyl)-N-phenylamino)biphenyl as a hole transporting material was formed first using a resistance heating method. Using H-1 as a host material and the compound [43] as a dopant material, a 35 nm thick layer having a doping concentration of 2% was formed. Then, a 20 nm thick layer of E-1 as an electron transporting material was laminated. The film thickness as referred to herein is the value displayed by a quartz crystal oscillator type film thickness monitor. Then, under vacuum, a mask comprising a Kovar® sheet with a thickness of 50 μm in which sixteen 250 μm apertures (remaining width 50 μm, corresponding to a 300 μm pitch) had been provided by wet etching is arranged such that the mask and ITO stripes are at right angles to each other, and this then fixed with a magnet from the underside so that the mask and ITO substrate were closely adhered to each other. After doping the organic layer with 0.5 nm of lithium, aluminum was vapor deposited in a thickness of 200 nm to produce a 32×16 dot matrix device. When the device was subject to matrix driving, characters were indicated without crosstalk.

The light emitting device material of the present invention can provide a light emitting device material that can be used for a light emitting device and the like and is excellent in fluorescence quantum yield. According to the present invention, a light emitting device that is high in luminance efficiency and excellent in at least one of color purity and durability is obtained. The light emitting device of the present invention can be applied to the fields of display elements, flat panel displays, backlights, illuminations, interiors, signs, billboards, electrophotographic machines, optical signal generators and the like.

What is claimed is:

1. A light emitting device material comprising a fluorene compound represented by the following general formula (1):

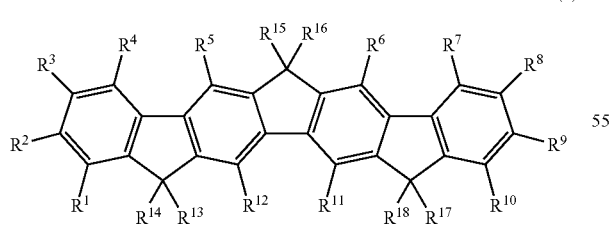

(1)

wherein $R^1$ to $R^{18}$ each may be the same or different and are selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, halogen, a cyano group, an amino group, a silyl group, and $-P(=O)R^{19}R^{20}$, $R^{19}$ and $R^{20}$ are each selected from the group consisting of an aryl group and a heteroaryl group, adjacent substituents among $R^1$ to $R^{18}$ may be combined with each other to form a ring, provided that at least one of $R^1$ to $R^{12}$ is a substituent represented by the following general formula (2):

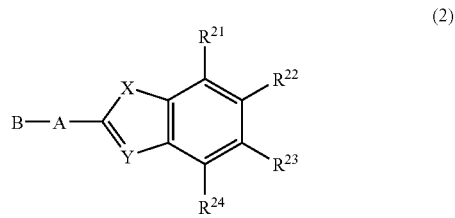

(2)

wherein $R^{21}$ to $R^{24}$ each may be the same or different and are selected from the group consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a cyano group, an amino group, and a silyl group, adjacent substituents among $R^{21}$ to $R^{24}$ may be combined with each other to form a ring, A is selected from the group consisting of a single bond, an arylene group, and a heteroarylene group, B is used for linkage to $R^1$ to $R^{12}$, X is an oxygen atom or a sulfur atom, Y is selected from among the following groups:

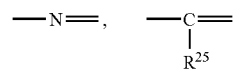

wherein $R^{25}$ is selected from the group consisting of hydrogen, an alkyl group, a cycloalkyl group, a heterocyclic group, an alkenyl group, a cycloalkenyl group, an alkynyl group, an aryl group, and a heteroaryl group.

2. The light emitting device material according to claim 1, wherein in the general formula (1), at least one of $R^1$ to $R^{12}$ is a group represented by the following general formula (3):

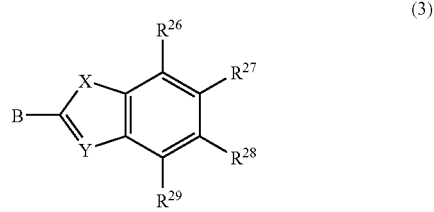

(3)

wherein $R^{26}$ to $R^{29}$ each may be the same or different and are selected from the croup consisting of hydrogen, an alkyl group, a cycloalkyl group, a heterocyclic group, an alkenyl group, a cycloalkenyl group, an alkynyl group, an alkoxy group, an alkylthio group, an aryl ether group, an aryl thioether group, an aryl group, a heteroaryl group, a cyano group, an amino group, and a silyl group, adjacent substituents among $R^{26}$ to $R^{29}$ may be combined with each other to form a ring, B is used for linkage to $R^1$ to $R^{12}$, X is an oxygen atom or a sulfur atom, Y is selected from among the following groups:

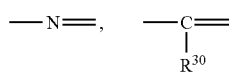

wherein $R^{30}$ is selected from the group consisting of hydrogen, an alkyl group, a cycloalkyl group, a heterocyclic group, an alkenyl group, a cycloalkenyl group, an alkynyl group, an aryl group, and a heteroaryl group.

3. The light emitting device material according to claim 2, wherein in the general formula (3), Y is a nitrogen atom.

4. The light emitting device materials according to claim 1, wherein at least one of $R^2$ and $R^9$ of the general formula (1) is a group represented by general formulae (2).

5. The light emitting device materials according to claim 1, wherein $R^{13}$ to $R^{18}$ of the general formula (1) are each selected from the group consisting of an alkyl group, an aryl group, and a heteroaryl group.

6. A light emitting device comprising an anode, a cathode, and at least an emissive layer located between the anode and the cathode and being capable of emitting light by electric energy, wherein the emissive layer includes the light emitting device material according to claim 1.

7. The light emitting device according to claim 6, wherein the emissive layer comprises a host material and a dopant material, and the light emitting device material containing a fluorene compound represented by the general formula (1) is the dopant material.

8. The light emitting device according to claim 6, wherein at least an electron transporting layer is present between the emissive layer and the cathode, the electron transporting layer contains a compound having a heteroaryl ring structure including electron-accepting nitrogen, and the compound having a heteroaryl ring structure is comprised of an element selected from the group consisting of carbon, hydrogen, nitrogen, oxygen, silicon, and phosphorus.

9. The light emitting device material according to claim 2, wherein at least one of $R^2$ and $R^9$ of the general formula (1) is a group represented by general formula (3).

\* \* \* \* \*